United States Patent
Manning et al.

(10) Patent No.: US 8,263,326 B2
(45) Date of Patent: Sep. 11, 2012

(54) COMPOUNDS AND METHODS FOR MODULATING ACTIVATION OF NF-κB

(75) Inventors: Anthony M. Manning, Lake St. Louis, MO (US); Frank Mercurio, San Diego, CA (US); Sharon Amit, Beer-Sheba (IL); Yinon Ben-Neriah, Zion (IL); Matti Davis, Jerusalem (IL); Ada Hatzubai, Kibutz Palmah-Zova (IL); Avraham Yaron, Jerusalem (IL); Irit Alkalay, Jerusalem (IL); Aaron Ciechanover, Haifa (IL)

(73) Assignee: Signal Pharmaceuticals, LLC, San Deigo, CA (US)

( * ) Notice: Subject to any disclaimer, the term of this patent is extended or adjusted under 35 U.S.C. 154(b) by 0 days.

(21) Appl. No.: 12/189,048

(22) Filed: Aug. 8, 2008

(65) Prior Publication Data

US 2009/0233855 A1    Sep. 17, 2009

Related U.S. Application Data

(60) Continuation of application No. 11/698,848, filed on Jan. 25, 2007, now Pat. No. 7,414,120, which is a continuation of application No. 10/665,715, filed on Sep. 19, 2003, now Pat. No. 7,186,503, which is a division of application No. 09/832,161, filed on Apr. 9, 2001, now Pat. No. 6,656,713, which is a continuation of application No. 09/210,060, filed on Dec. 10, 1998, now abandoned.

(51) Int. Cl.
*C12Q 1/25* (2006.01)
*C12N 9/00* (2006.01)

(52) U.S. Cl. ............................. 435/4; 435/189
(58) Field of Classification Search ................. None
See application file for complete search history.

(56) References Cited

U.S. PATENT DOCUMENTS

| | | | |
|---|---|---|---|
| 5,126,324 A | 6/1992 | Clark | |
| 5,519,003 A | 5/1996 | Mochly-Rosen et al. | |
| 5,597,898 A | 1/1997 | Ghosh | |
| 5,849,580 A | 12/1998 | Ghosh | |
| 5,851,812 A | 12/1998 | Goeddel et al. | |
| 5,916,760 A | 6/1999 | Goeddel | |
| 5,932,425 A | 8/1999 | Alkalay et al. | |
| 5,939,302 A | 8/1999 | Goeddel | |
| 5,972,674 A | 10/1999 | Mercurio | |
| 6,232,081 B1 * | 5/2001 | Harper et al. | 435/7.1 |
| 6,235,492 B1 | 5/2001 | Rothe | |
| 6,235,512 B1 | 5/2001 | Rothe | |
| 6,235,513 B1 | 5/2001 | Rothe | |
| 6,242,253 B1 | 6/2001 | Karin | |
| 6,258,579 B1 | 7/2001 | Mercurio | |
| 6,410,516 B1 | 6/2002 | Baltimore | |
| 6,479,266 B1 | 11/2002 | Rothe | |
| 6,576,437 B2 | 6/2003 | Mercurio | |
| 6,649,654 B1 | 11/2003 | Karin | |
| 6,656,713 B2 | 12/2003 | Manning | |
| 7,186,503 B2 | 3/2007 | Manning | |
| 7,285,654 B2 | 10/2007 | Mercurio | |
| 7,414,120 B2 | 8/2008 | Manning | |

FOREIGN PATENT DOCUMENTS

| | | |
|---|---|---|
| WO | WO 98/36070 | 8/1998 |
| WO | WO 99/38969 | 8/1999 |

OTHER PUBLICATIONS

F. Margottin et al. "A Novel Human WD Protein h-βTrCP that Interacts with HIV-1 Vpu Connects CD4 to the ER Degradation Pathway Through an F-Box Motif", Molecular Cell 1:565-574 (Mar. 1998).*
Alkalay et al., "In vivo Stimulation of IkB Phosphorylation is Not Sufficient to Activate NF-kB," Molecular and Cellular Biology 15(3):1294-1301 (1995).
Ciechanover, "The Ubiquitin-Proteasome Proteolytic Pathway," Cell 79:13-21, 1994.
DiDonato et al., "Mapping of the Inducible IkB Phosphorylation Sites That Signal Its Ubiquitination and Degradation," Molecular and Cellular Biology 16(4):1295-1304 (1996).
Gura et al., Science, 278:1041-1042, 1997.
Ishikawa et al., "Prediction of Coding Sequences of Unidentifed Human Genes X. The Complete Sequences of 100 New cDNA Clones from Brain which Code Large Proteins in vitro," DNA Research 5:169-176, Jun. 30, 1998.
Margottin et al., A Novel Human WD Protein, h-beta TrCP, that interacts with HIC-I Vpu Connects CD4 to the ER Degradation Pathway through the F-Box Motif, Molecular Cell 1:565-574, 1998.
Margottin et al., A Novel Human WD Protein, h-beta TrCP, that interacts with HIC-I Vpu Connects CD4 to the ER Degradation Pathway through the F-Box Motif, Genbank Database, Accession No. Y14153, Mar. 28, 1998.
Ohara, et al., "*Homo sapiens* mRNA for KIAA0696 protein, partial cpds.," EMBL Database, Accession No. AB14596, 1998.
Yaron et al., "Identification of the receptor component of the 1kappaBalpha-ubiquitin ligase," Nature 396(6711):590-594, Dec. 10, 1998.
Yaron et at, Genbank Database, Accession No. AF101784, 1999.
Yaron et al., Genbank Database, Accession No. AF099932, 1999.
Yaron et al., "Inhibition of NF-kappaB cellular function via specific targeting of the 1 kappa B-ubiquitin ligase," EMBO Journal, 16(21):6486-6494, 1997.

* cited by examiner

*Primary Examiner* — Rebecca Prouty
(74) *Attorney, Agent, or Firm* — Jones Day

(57) ABSTRACT

Compositions and methods for modulating the activation of nuclear factor κB (NF-κB) are provided. The compositions comprise one or more agents that modulate ubiquitination of phosphorylated IκBα and/or IκBβ. Such compositions may be used for treating diseases associated with NF-κB activation. Modulating agents include human E3 ubiquitin ligases, antibodies thereto and variants thereof, as well as related proteins.

5 Claims, 16 Drawing Sheets

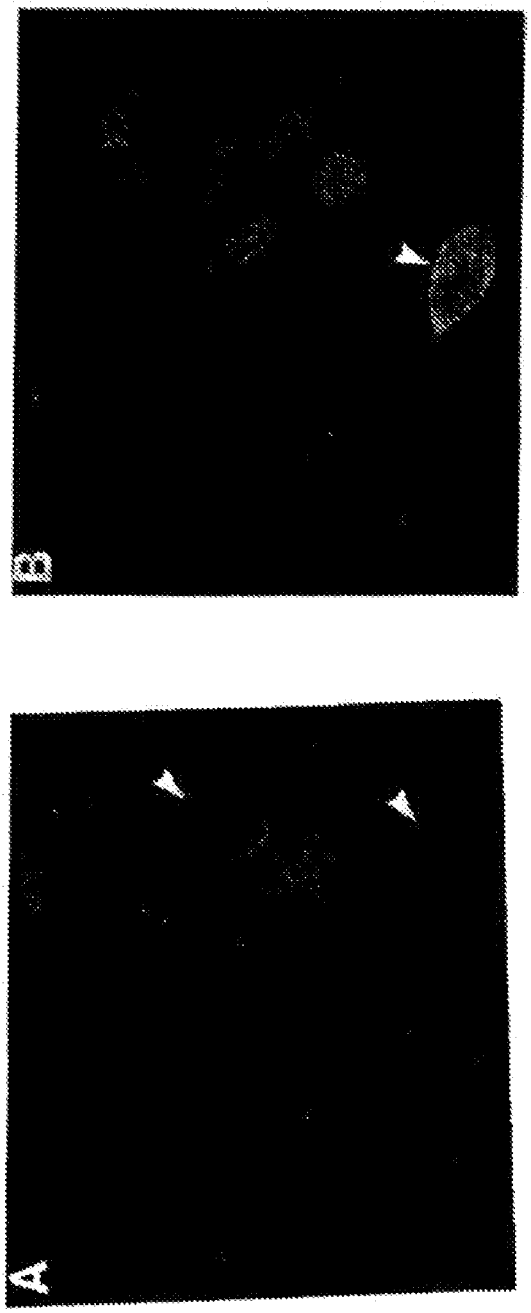
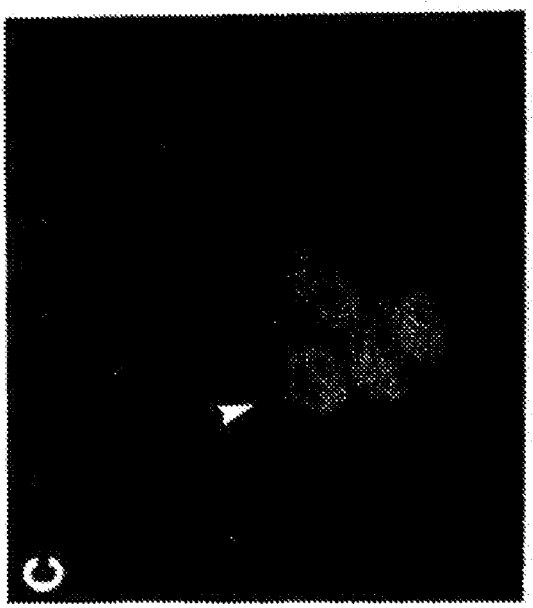
FIG. 4A-4C

```
GCGAGGCGGGGCCGCCGGGGCCGCCATGGAGCCCGACTCGGTGATTGAGGACAAGACCATCGAGCTCATGTGTTCTGTGC
CAAGGTCTTTGTGGCTAGGCTGCGCCAACCTGGTAGAGAGCATGTGCGCACTGAGTTGCC
TGCAGAGCATGCCCAGTGTCAGATGTCTCCAGATAAGTAATGGAACATCATCTGTGATCGTCTCCAGAAA
GAGGCCATCAGAAGGAAACTATCAAAAAGAAAAAGACTTGTGTATTAAATATTTTGACCAGTGGTCTGAA
TCAGATCAAGTGGAATTTGTGGAACATCTTATTTCACGAATGTGTCATTATCAGCATGGACATATTAACT
CTTACCTGAAGCCCATGTTGCAGCGGGACTTTATTACCGCTTTACCAGAGCAAGGCTTAGATCACATAGC
AGAAAACATTCTTTCGTACCTGGATGCCAGGTCTCTGTGTGCAGCAGAGCTGGTATGTAAAGAATGGCAG
CGAGTGATCTCAGAAGGAATGCTTTGGAAGAAGCTGATTGAACGAATGGTACGCACTCATCCCCTATGGA
AAGGACTTTCAGAAAGAAGAGGGTGGGATCAGTACCTGTTTAAAAACAGACCCACAGATGGCCCTCCAAA
TTCATTTTATAGGTCATTATACCCAAAGATTATCCAGGATATAGAGACTATAGAATCTAACTGGCGGTGT
GGACGACACAACTTGCAGAGGATTCAGTGCCGCTCTGAAAATAGTAAAGGTGTCTACTGTTTACAGTACG
ATGATGAAAAAATTATCAGTGGCCTACGAGATAATTCTATTAAGATATGGGATAAAACCAGCCTGGAATG
TTTGAAAGTGTTAACAGGACACACAGGCTCTGTCCTCTGTCTGCAGTATGATGAGCGTGTCATTGTAACT
GGCTCTTCAGATTCTACGGTGAGAGTGTGGGATGTGAACACGGGTGAAGTTCTTAACACATTGATCCACC
ACAATGAGGCTGTATTGCACTTACGCTTCAGCAATGGACTGATGGTGACCTGTTCCAAGGACCGCTCCAT
TGCTGTGTGGGACATGGCTTCTGCGACCGACATCACTTTACGCCGTGTCCTGGTTGGCCACCGGGCTGCC
GTCAATGTAGTAGACTTTGACGACAAGTACATCGTGTCTGCCTCTGGTGACAGGACCATCAAAGTCTCGA
GCACGAGCACCTGTGAATTTGTTCGTACTCTCAATGGGCACAAGCGGGGCATTGCCTGTCTCCAGTACAG
GGATCGCCTGGTTGTTAGTGGATCATCAGATAATACCATTAGGCTCTGGGATATTGAATGTGGTGCCTGT
TTAAGAGTCCTAGAGGGACATGAAGAATTGGTCCGATGCATCCGGTTTGATAACAAGAGGATTGTCAGTG
GGGCCTATGATGGGAAAATTAAAGTTTGGGACTTGCAAGCTGCTCTTGACCCTCGAGCCCCAGCAAGCAC
ATTGTGTTTGCGCACATTGGTGGAACATTCTGGACGTGTGTTTCGGCTCCAGTTTGATGAGTTTCAGATC
ATCAGCAGCTCCCATGATGACACTATTTTGATTTGGGATTTCTTAAATGTGCCTCCCAGTGCCCAGAATG
AGACCCGTTCTCCCTCCAGAACATACACTTACATCTCTAGATAACAGTCTGCACTTTCACCCGTTTCAGG
GTTTTCTAGTCTTGAACTACTGGCTACGTGGCTACCAAATGCCTAAGGGAGTTCGTTCACAGCTGAGTTA
TGAAGCTGGAATTGGTTCTAGACGCTGGGTAGATGCAAAGCAGCCTAACTCTTCAAGTACCGACATTTCT
CACCTCTGATTCCGGCTCTCCTTTGAGAAGGAGACCTTAGCTTCCCCGGCTTCAAGTAGAACAGAAGCCC
GTTTCCTTCCCTCATCAGTGAAAAAATCTAATGTTTCAAATGTAAATTGTTCATAGAAAAGGAACATAGA
ATCTGTTTTACAGAAGTAAATCGACCGTCAAGAGAAGACTTGGCCTCTAATTTATATTGCTTTGCACTTT
GGTTTGATATTAAGAAACAGCATTCTTCTTCAGTGAAATTTTGGGTGCCAAACACCTACCCAGAATGTCC
AGGGCTTTCATTTTCAAAAGTTAGCATTCTCCTTTTGACCGTCCAAGTCATTATGAATTCTGACTTGTTG
TATTAGGAACATGTTGGACAGTGGAAAATTTTCTCTGGATTGTTTTAGTAATATTTTTGGGATTATACTT
CCTTTCTGTACCAATTTCTTTTAATTTAAAGAACTATAAGTCAGTTATATTATCTACCAACAGGTAATAT
AGCTCTTTCTTTTATTAACTGTTCTCTGTCCCCCAACCATCTCCTGATATTTGGTAGAGTAACACCTTTA
TACGTGTGCTTGCCTCCTAATTTAAAATACTGTATTCGCATGTAGATATAATGTACATAACAGTTTAACC
TCAAAGTTGCTGGAGTCAGGGCCCCCTGTGCTTGAGACACTAATACAGAGTGTGTTCGCACTTAGCCATG
GGCTGGGCTCAAGAACCTGATACCTGGGTTGATGTGGATTACCTAGAACCCTTCCTGCAGTATTCATACA
GTGTTTTTATTTTGTTGTTGTCATTGCGTGTGTGTGGTTTGTGTGTGTTTTTAATGAGAATCTTGTTTTA
AAATGTAATTTCTAAGGTTTAACACCAAAATGTTTTATTTGTTGTGGAGTATATATTATACAATAGAGAG
GTACCTTAAACATTTTTTGTTCTTATTCTTTTTCTCATAAGTACTCCTGAGTACAAGTGGTCACCTCCCA
TAGTATTCATTTGGCTTCGCTGTCAAAAATCATTATTCTGTGCAGTCGTGGCCCTGGGCAAGGGGAAATAA
GAAGGCCCTGTTGACGGGCTGTCTTGGCTCTGGAATTCATGCATCCTGGCCTTGCCAAGGTTCTGGCAGG
GCCTGCTGGTGTGTTGGAGCCTGCAGGGCAGGTCAGGCTGGTTCAGAGGCCCATGCTGAGGGGTGGGTGC
TCTGAAGTGGAGTGAAGCCTCAAGCCCATGAATGCCACCCCAGTCATCTCTGGTGTCAGCTGCTGCTGTG
GCCCCAGCAGGTTCTCAAAGCTCCCAAGTCCTCCCTACGACACAGCCCAAATGTGTAAATGGCACTGTTG
CCCTGACAGTGCATGGAAAGGACGTTGGCATCCAATTGGCACTCCTTCTCCCTTATTCAATATTAGGTTT
GATTTGCCCTTCGCCATTGTTTCCAAAGATCAAGGAATGTCAATAACATTTTAAAGGACCAATAAACAGC
CTCCTATAAAGTAAACCTCTTCCCGTGGAAGCACACTCTACTACTAAAGGGAAGGCCCCTGGGCTCTGAT
TTGTCCTTTGCATTGAGAACGGTGTGGGGATCAGTGTGTGTGTATGTGATTTGTTTATTGAGTTGGCTTT
GCTTTTTTAGTTTTTCTTTTAAAAATAAAATCCTTCCTTCCCATGTTACTAAATTAATTTATGTTTTTGA
GAGGTTGAGTCTCAAAGTGTAAACAATAAACCTCCATTCATAAGGTGGATGTTGTAAGCTTGATGGTGGT
TGTGAAAGTGATTTAGCTTTGACCACTTTTCATCCTACAGCTTCAATATCAAACTGGTTAGGAAAGCCCA
GGGGGAAGGGAGGGGGCAGGGGAGGAGGCAATTCTGAATGAATGAATGGATTTTTTGTTGTTTTTGCATG
TTTAATATAGAAGTTCCCCTCGTTCCTTGGGAGATGATGGCCTTTGAATATGCAGACAACCTTTGAATTG
```

*FIG. 9A*

```
TGCCTACTAAATTATAGCAGGGGACTTTGGCACCCAAGGAGTTCTGACTTTCTGGGATTATAATAGTAAT
TCCCAGCCATACTCTGGACTTTATTTTGCTAACCATAACTGAGCAAATGTAAATTACTGCTATATTAATG
TTTTAAAGCACTGGGATAGTCTAATTCTAACTTGTAATTAATTATGTTTGCCAATTATCTGTTTGAAATA
AATTTGTGTCTGAACAGCTATTGAAACTGTTAAATTGTACAGATATTATTCATGACAGCTTTGTACTGTG
GAATGTGCTTAATAAAAAACAAAAAAGTTTGACTTTTGTCCAGTAAATTGCTAAGTAATGTCAATAAATC
GAGTATGGGTATTATGCAGTGCACCTAATCTGGCTTCATGCAATTGTTACTTCAGCTACTGATTCAAAGC
CAATACTCTTAATAAAGTGTTGCAATACTC
```

*FIG. 9B*

MEPDSVIEDKTIELMCSVPRSLWLGCANLVESMCALSCLQSMPSVRCLQISNGTSSVIVSRK
RPSEGNYQKEKDLCIKYFDQWSESDQVEFVEHLISRMCHYQHGHINSYLKPMLQRDFITALPEQGLDHIA
ENILSYLDARSLCAAELVCKEWQRVISEGMLWKKLIERMVRTDPLWKGLSERRGWDQYLFKNRPTDGPPN
SFYRSLYPKIIQDIETIESNWRCGRHNLQRIQCRSENSKGVYCLQYDDEKIISGLRDNSIKIWDKTSLEC
LKVLTGHTGSVLCLQYDERVIVTGSSDSTVRVWDVNTGEVLNTLIHHNEAVLHLRFSNGLMVTCSKDRSI
AVWDMASATDITLRRVLVGHRAAVNVVDFDDKYIVSASGDRTIKVWSTSTCEFVRTLNGHKRGIACLQYR
DRLVVSGSSDNTIRLWDIECGACLRVLEGHEELVRCIRFDNKRIVSGAYDGKIKVWDLQAALDPRAPAST
LCLRTLVEHSGRVFRLQFDEFQIISSSHDDTILIWDFLNVPPSAQNETRSPSRTYTYISR

COMPOUNDS AND METHODS FOR MODULATING ACTIVATION OF NF-κB

This application is a continuation of U.S. application Ser. No. 11/698,848, filed Jan. 25, 2007, now U.S. Pat. No. 7,414,120, which is a continuation of U.S. application Ser. No. 10/665,715, filed Sep. 19, 2003, now U.S. Pat. No. 7,186,503, which is a division of U.S. application Ser. No. 09/832,161, filed Apr. 9, 2001, now U.S. Pat. No. 6,656,713, which is a continuation of U.S. application Ser. No. 09/210,060, filed Dec. 10, 1998, now abandoned, each of which is incorporated hereby by reference in its entirety.

TECHNICAL FIELD

The present invention relates generally to compositions and methods for modulating the activation of nuclear factor κB (NF-κB). The invention is more particularly related to agents that modulate ubiquitination of phosphorylated IκBα and/or IκBβ and to methods for treating diseases associated with NF-κB activation. Modulating agents encompassed by the present invention include E3 ubiquitin ligases, and portions and variants thereof.

BACKGROUND OF THE INVENTION

NF-κB is a transcription factor that plays a pivotal role in the highly specific pattern of gene expression observed for immune, inflammatory and acute phase response genes, including interleukin 1, interleukin 8, tumor necrosis factor and certain cell adhesion molecules. Like other members of the Rel family of transcriptional activators, NF-κB is sequestered in an inactive form in the cytoplasm of most cell types. A variety of extracellular stimuli including mitogens, cytokines, antigens, stress inducing agents, UV light and viral proteins initiate a signal transduction pathway that ultimately leads to NF-κB release and activation.

Important modulators of NF-κB activation are the inhibitor proteins IκBα and IκBβ (referred to herein as IκB), which associate with (and thereby inactivate; NF-κB in the cytoplasm of nonstimulated cells. Activation and nuclear translocation of NF-κB occurs following signal-induced phosphorylation of IκB, which leads to proteolysis via the ubiquitin pathway. For IκBα, the stimulus-induced phosphorylation at serines 32 and 36 renders the inhibitor a target for ubiquitination at lysines 21 and 22, resulting in degradation. Similarly, phosphorylation of IκBβ at serines 19 and 23 renders the inhibitor a target for ubiquitination at lysine 9. However, the component(s) of the ubiquitin system mediating IκB recognition have not been identified.

Degradation of a protein via the ubiquitin pathway proceeds by two discrete and successive steps: (a) covalent attachment of multiple ubiquitin molecules to the protein substrate, and (b) degradation of the targeted protein by the 26S proteasome complex. The ubiquitin pathway consists of several components that act in concert and in a hierarchical manner (for reviews, see Ciechanover, *Cell* 79:13, 1994; Hochstrasser, *Curr. Op. Cell. Biol.* 7:215, 1995; Jentsch and Schienker, *Cell* 52:881, 1995; Deshaies, *Trends Cell Biol.* 5:428, 1995). One such component, a single E1 enzyme, carries out activation of ubiquitin. Several major species of E2 enzymes have been characterized in mammalian cells, plants, and yeast. E2 enzymes probably bind to the ligase E3 (Reiss and Hersko, *J. Biol. Chem.* 255:3685, 1990; Dohmen et al., *Proc. Natl. Acad. Sci. USA* 88:7351, 1991) and it appears that each E2 enzyme can act with one or more E3 proteins (Nuber et al., *J. Biol. Chem.* 277:2795, 1996; Orian et al., *J. Biol. Chem.* 270:21707, 1995; Stancovski et al., *Mol. Cell. Biol.* 75:7106, 1995; Gonen et al., *J. Biol. Chem.* 270:302, 1996).

Only few E3 enzymes (ubiquitin ligases) have been described. Mammalian E3α (UBR1 in yeast) and E3β recognize protein substrates via their free N-terminal amino acid residues ("N-end rule"; Varshavsky, *Cell* 69:725, 1992; Hershko and Ciechanover, *Ann. Rev. Biochem.* 61:761, 1992). Cdc53 is probably an E3 involved in targeting phosphorylated G1 cyclins (Willems et al., *Cell* 86:453, 1996). E6-AP is involved in recognition of p53 (Scheffner et al., *Cell* 75:495, 1993), and a series of unique E6-AP homologous proteins have been identified (Huibregtse et al., *Proc. Natl. Acad. Sci. USA* 92:2563, 1995): Nedd4 is involved the degradation of the epithelial Na⁻ channel (Staub et al, *Embo J.* 75:2371, 1996) and RSP5 (NIP1) is involved in tagging the permeases Gap1 and Fur1 (Hein et al., *Mol. Microbiol.* 18:11, 1995), whereas Pub1 targets Cdc25 (Nefsky and Beach, *EMBO J.* 75:1301, 1996). Several other E3 enzymes that have been recently isolated appear to be involved in the degradation of c-Fos, a subset of muscle proteins, and in the processing of p105, the NF-κB precursor (Orian et al., *J. Biol. Chem.* 270:21707, 1995; Stancovski et al., *Mol. Cell. Biol.* 75:7106, 1995; Gonen et al. *J. Biol. Chem.* 277:302, 1996). Thus, it appears that the ligases represent a large, mostly unraveled family of enzymes and, except for the mode of recognition of the "N-end rule" ligases (E3α and E3β), the recognition motifs of all other known substrates of the ubiquitin system have not been identified.

Accordingly, there is a need in the art for an improved understanding of IκB degradation via the ubiquitin pathway, and for the identification of modulators of this degradation process for use in treating diseases associated with activation of NF-κB. The present invention fulfills these needs and further provides other related advantages.

SUMMARY OF THE INVENTION

Briefly stated, the present invention provides compositions and methods for modulating the activation of nuclear factor κB (NF-κB) by modulating ubiquitination of phosphorylated IκBα and/or IκBβ. Within one aspect, the present invention provides isolated human E3 ubiquitin ligase polypeptides. Such polypeptides may comprise a human E3 ubiquitin ligase sequence as recited in SEQ ID NO: 16, or a portion or variant thereof that differs in one or more amino acid substitutions, insertions, deletions and/or additions, such that the polypeptide (a) enhances ubiquitination of phosphorylated IκB or (b) binds to phosphorylated IκB and inhibits ubiquitination of phosphorylated IκB. Within certain embodiments, such a polypeptide may have the sequence recited in SEQ ID NO: 16 or a variant thereof that differs in one or more amino acid deletions, insertions or substitutions at no more than 20% of the amino acid residues in SEQ ID NO: 16, such that the polypeptide enhances ubiquitination of phosphorylated IκB. Within further embodiments, such a polypeptide may comprise a portion of a human E3 ubiquitin ligase, or variant of such a portion, wherein the portion binds to phosphorylated IκB and inhibits ubiquitination of phosphorylated IκB.

The present invention further provides, within other aspects, isolated polynucleotides that encode a polypeptide as described above. Within certain embodiments, such polynucleotides may encode a portion of a human E3 ubiquitin ligase, or variant of such a portion, as described above. Antisense polynucleotides comprising at least 10 consecutive nucleotides complementary to such a polynucleotide are also provided. Expression vectors comprising such a polynucleotide, and host cells transformed or transfected with such an expression vector, are further provided.

Within further aspects, the present invention provides pharmaceutical compositions comprising a polypeptide or polynucleotide as described above in combination with a physiologically acceptable carrier.

Within other aspects, the present invention provides isolated antibodies, and antigen binding fragments thereof, that bind to a human E3 ubiquitin ligase having a sequence recited in SEQ ID NO: 16. Such antibodies may be monoclonal.

Within further aspects, pharmaceutical compositions are provided, comprising an antibody or fragment thereof as described above in combination with a physiologically acceptable carrier.

The present invention further provides methods for modulating NF-κB activity in a patient, comprising administering to a patient a pharmaceutical composition as described above.

Within further aspects, the present invention provides methods for treating a patient afflicted with a disorder associated with NF-κB activation, comprising administering to a patient a therapeutically effective amount of a pharmaceutical composition as described above, and thereby treating a disorder associated with NF-κB activation. Such disorders include inflammatory diseases, autoimmune diseases, cancer and viral infection.

Within further aspects, the present invention provides methods for screening for an agent that modulates NF-κB activity, comprising the steps of: (a) contacting a candidate agent with a human E3 ubiquitin ligase polypeptide, wherein the polypeptide comprises a sequence recited in SEQ ID NO: 16 or a portion or variant thereof that differs in one or more amino acid substitutions, insertions, deletions or additions, such that the polypeptide enhances ubiquitination of phosphorylated IκB, under conditions and for a time sufficient to permit interaction between the polypeptide and candidate agent; and (b) subsequently evaluating the ability of the polypeptide to enhance ubiquitination of phosphorylated IκB, relative to a predetermined ability of the polypeptide to enhance ubiquitination of phosphorylated IκB in the absence of candidate agent; and therefrom identifying an agent that modulates NF-κB activity. Candidate agents for use within such screens include, but are not limited to, small molecules present within a combinatorial library.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

In FIG. 1A, lane 1 shows the ubiquitination of an IκBα polypeptide that contains alanine residues at positions 32 and 36 (S32/36A; SEQ ID NO: 13) and lane 2 shows the ubiquitination of a non-phosphorylated wild-type IκBα polypeptide (SEQ ID NO: 12). In lanes 3-14, the ubiquitination substrate was wild-type IκBα (SEQ ID NO: 12). In lane 3, ubiquitination was performed in the absence of ATP; and in lanes 4-14 the reaction was performed in the presence of ATPγS with (lanes 5-14) or without (lane 4) an IκB E3 recognition motif or other peptide. The peptides shown are: 400 μM c-Fos phosphopeptide (ppFos (SEQ ID NO: 10), lane 5); 400 μM serine 32, 36 to alanine substituted IκBα peptide (pp21S/A (SEQ ID NO: 11), lane 6); 40 μM doubly phosphorylated IκBα peptide (pp21 (SEQ ID NO:9), lane 7); 400 μM non-phosphorylated IκBα peptide (p21 (SEQ ID NO:9), lane 8); 100 μM singly phosphorylated IκBα peptides (ppS32 (SEQ ID NO:9), lane 9: ppS36 (SEQ ID NO:9), lane 10); and 40 μM shorter, doubly phosphorylated IκBα peptides (pp19 (SEQ ID NO:8), lane 11): pp15 (SEQ ID NO:7), lane 12; pp11 (SEQ ID NO:6), lane 13; pp7 (SEQ ID NO:5), lane 14).

In FIG. 1B, the ubiquitination substrate was free wild type IκBα (SEQ ID NO: 12, lanes 1-3) or free S32/36A substituted IκBα (SEQ ID NO: 13, lanes 4-6). The reaction was performed in the absence (lanes 1 and 4) or presence (lanes 2, 3, 5 and 6) of ATPγS. 40 μM doubly phosphorylated IκBα peptide (pp21 (SEQ ID NO:9) was added to the conjugation reaction mixture in the samples shown in lanes 3 and 6.

In FIG. 1C, the ubiquitination of bulk cellular proteins in HeLa extract is shown. Lane 1 shows the ubiquitination in the absence of ATP, and lane 5 shows the ubiquitination in the presence of ATP. In lanes 3-5, an IκB E3 recognition motif or other peptide was added: 40 μM doubly phosphorylated IκBα peptide (pp21 (SEQ ID NO:9), lane 2); 400 μM c-Fos phosphopeptide (ppFos (SEQ ID NO: 10), lane 3); and 400 μM non-phosphorylated IκBα peptide (p21 (SEQ ID NO:9), lane 4).

In FIG. 1D, the ubiquitination substrate was phosphorylated (lanes 2-7) or non-phosphorylated (lane 1) wild type IκBβ (SEQ ID NO:14). Reactions were performed in the absence (lane 2) or presence (lanes 1, 3-7) of ATPγS, and with (lanes 4-7) or without (lanes 1-3) an IκB E3 recognition motif or other peptide. The peptides shown are: 40 μM doubly phosphorylated IκBα peptide (pp21 (SEQ ID NO:9), lane 4); 400 μM c-Fos phosphopeptide (ppFos (SEQ ID NO: 10), lane 5); 40 μM doubly phosphorylated IκBα peptide (pp19 (SEQ ID NO:8), lane 6); and 400 μM non-phosphorylated IκBα peptide (p21 (SEQ ID NO:9), lane 7).

FIGS. 4A-4F are micrographs showing the effect of candidate modulating agents on nuclear NF-κB translocation. In FIGS. 4A-C, pp21 (FIGS. 4A and 4B) or ppFos (FIG. 4C) was microinjected into the cytoplasm of HeLa cells. Cells were then activated immediately with TNFα and immunostained with anti-p65 antibodies. In FIGS. 4D-F. pp21 (FIG. 4D) or ppFos (FIG. 4F) was injected into the cytoplasm of human vascular endothelial cells (HUVEC). Cells were then activated immediately with TNFα and immunostained with anti-E-selectin antibodies. FIG. 4E is a phase contrast photograph of FIG. 4D. In each micrograph, the injected cells are marked by large arrows. A non-injected, E-selectin negative cell is marked by a small arrow in FIGS. 4D and 4E.

In FIG. 4G, the percent of HeLa cells displaying nuclear p65 staining is shown. 90 and 42 cells were microinjected with pp21 and ppFos, respectively. FIG. 4H shows the percent of HUVEC displaying E-selectin staining. 160 and 36 cells were microinjected with pp21 and ppFos, respectively. For each graph, column 1 shows the level in the absence of an IκB E3 recognition motif or other peptide and TNFα activation. Columns 2-4 show the level following TNFα activation in the absence of peptide (column 2) or in the presence of pp21 (column 3) or ppFos (column 4).

FIG. 7A is a photograph showing Colloidal Blue staining of SDS-polyacrylamide gel samples of immunopurified fractions containing IκBα/NF-κB and associated proteins. IκBα/NF-κB complex was phosphorylated by IKK-2EE (lanes 2, 3) or mock-phosphorylated and used to adsorb the ubiquitin-ligase from HeLa lysate (lanes 1, 2). Molecular-size markers (κD) are indicated on the right. Proteins identified by mass-spectrometry analysis are indicated on the left. Gel-sites corresponding to the bands associated with the ubiquitin-ligase activity (p54 and p58) are marked on the left by brackets. FIG. 7B is an autoradiogram of proteins adsorbed onto pIκBα/NF-κB from $^{35}$S-labeled HeLa cells. Radiolabeled HeLa lysate was incubated with IKK-phosphorylated antibody-immobilized IκBcc/NF-κB complex. The immune-complexes were then washed, eluted and analyzed by SDS-PAGE and autoradiography. Lane 1 shows non-phosphorylated IκBα/NF-κB complex incubated with HeLa lysate; lanes 2-4 show phosphorylated IκBα/NF-κB-complex incubated with HeLa lysate in the absence (lane 2) or presence of pIκBα-peptide (lane 3) or serine-substituted IκBα-peptide (lane 4). Indicated on the left are molecular size markers (κD), Rel A and IκBα bands; indicated in the right are the four pIκBα-associated bands, three of which were displaced by the pIκBα peptide (arrows).

FIG. 8A shows a nano-electrospray mass spectrum of the unseparated tryptic peptide mixture from the 54 κD gel band excised from a ligase-positive lane (equivalent to lane 2 in FIG. 7B). Peaks marked by arrows were fragmented and identified as peptides derived from β-TrCP. The bar indicates the region enlarged in C. FIGS. 8B and 8C present a comparison of the nanoelectrospray spectra of the 54 κD band associated with (C) and without (B) ubiquitin-ligase activity. The peptide at m/z 714.38 was selected for sequencing. FIG. 8D is a fragmentation spectrum of the peptide identified in FIG. 8C. A sequence tag was assembled from a series of doubly charged fragment ions and searched in the nrdb data-base for a matching pattern. Fragment masses calculated for the retrieved β-TrCP sequence AAVNVVDFDDKYIVSASGDR (SEQ ID NO:20) were compared with the complete fragmentation spectrum to confirm the match. Peaks matching expected fragment ions are marked by circles.

FIGS. 9A and 9B present the sequence of a polynucleotide encoding a human E3 ubiquitin ligase (SEQ ID NO: 15).

FIG. 10 presents a human E3 ubiquitin ligase protein sequence (SEQ ID NO: 16).

FIG. 11A illustrates selective binding to pIκBα. Proteins were immunoprecipitated through a FLAG epitope from transfected 293T cells, incubated with immunopurified IκBα/NF-κB complex, which had been treated (−/+IKK) as indicated and the bound material was analyzed by Western blotting with the indicated antibodies. The top panel shows specific pIκBα binding; the middle panel shows 10% of the substrate flow-through; the bottom panel is a blot of the immunoprecipitated proteins; and molecular size markers (κD) are indicated on the left. FIG. 11B shows that β-TrCP-pIκBα binding is abrogated by a phosphopeptide representing the pIκBα degradation motif[1] (pp10), but not by a related non-phosphorylated peptide (pS/A). FIG. 11C illustrates in vitro ubiquitination of pIκBα by the E3 family member proteins. Immunopurified FLAG-tagged proteins were incubated with $^{35}$S-labeled IκBα/NF-κB complexes, treated (−/+IKK) as indicated and subject to ubiquitination in the presence of ATPγS, ubiquitin, E1 and UBC5C. The IκBα substrate (composed of full-length and two degradation products), pIκBα-polyubiquitin conjugates and molecular size markers are indicated on the left.

FIG. 12A is a graph depicting the results of a κB-dependent luciferase assay in P/I-stimulated Jurkat cells transfected with κB-Luc reporter plasmid and the indicated expression vectors (i.e., from left to right, vector alone, vector encoding human β-TrCP, vector encoding human β-TrCP with a deletion of the F box region and vector encoding Drosophila Slimb protein). NF-κB activity is shown as relative (fold) luciferase activity, the non-stimulated empty FLAG vector being the reference (single-fold). FIG. 12B depicts the results of western blot analysis of IκBα of phorbol-ester and Ca$^{++}$ ionophore [P/I]-stimulated and non-stimulated Jurkat cells transfected with an empty FLAG vector or Δβ-TrCP. The post-stimulation interval (min) is indicated.

DETAILED DESCRIPTION OF THE INVENTION

Figure 1A:
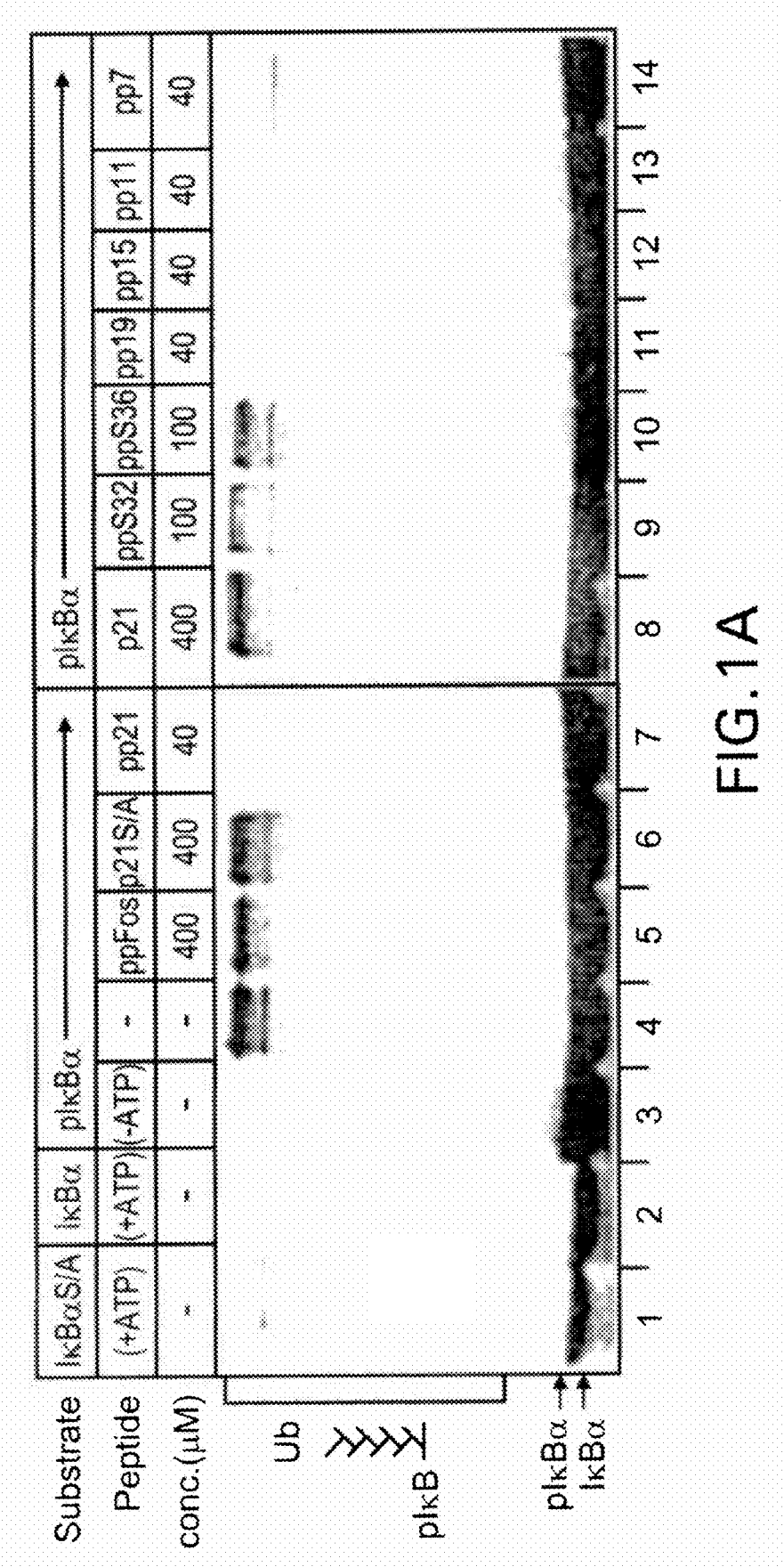
FIGS. 1A-1D are autoradiograms depicting the results of SDS-PAGE analysis of ubiquitination assays performed in the presence and absence of various IκB E3 recognition motifs. Unless otherwise indicated, the substrate was an $^{35}$S-labeled, HA-tagged IκB polypeptide that was phosphorylated and NF-κB complex-associated.

As noted above, the present invention is generally directed to compositions and methods useful for modulating the activation of nuclear factor κB (NF-κB) and for treating diseases associated with such activation. In particular, the invention is directed to agents that modulate ubiquitination of phosphorylated IκB (i.e., IκBα and/or IκBβ). Such ubiquitination results in the release and activation of NF-κB.

The present invention is based, in part, on the identification and characterization of a human E3 ubiquitin ligase that recognizes phosphorylated and NF-κB-associated IκB. Polypeptides comprising this E3 ubiquitin ligase, as well as portions and other variants thereof, may be used to modulate NF-κB activity in vitro or in a patient. Such polypeptides may also be used, for example, to identify agents (such as small molecules) that may be used to modulate NF-κB activity, and to treat disorders associated with abnormal NF-κB activation. Human E3 Ubiquitin Ligase Polypeptides and Polynucleotides It has been found, within the context of the present invention, that a human E3 ubiquitin ligase that migrates as a 54 kD protein binds to, and enhances ubiquitination of, phosphorylated IκBα (phosphorylated IκBα is also designated herein as pIκBα). The sequence of a polynucleotide encoding a human E3 ubiquitin ligase is provided in FIG. 9 and SEQ ID NO: 15; and a full length human E3 ubiquitin ligase protein sequence is provided in FIG. 10 and SEQ ID NO: 16. Human E3 ubiquitin ligase has also been found, within the context of the present invention, to be a member of a family of F-box/WD proteins that includes β-TrCP (Margottin et al., *Mol. Cell* 7:565-574, 1998) and the Drosophila Slimb protein (see Jiang and Struhl, *Nature* 597:493-496, 1998). As described in greater detail below, other members of this family share certain properties of E3, and such proteins and variants thereof may be used within certain methods provided herein for E3.

Human E3 ubiquitin ligase polypeptides encompassed by the present invention include native human E3 ubiquitin ligase (also referred to herein as "E3"), as well as portions and other variants thereof. Variants of E3 may differ in sequence from native E3 due to one or more amino acid substitutions, deletions, additions and/or insertions, as described herein, provided that the variant binds to and enhances ubiquitination of an IκB polypeptide as described herein. Preferably, a variant of E3 contains amino acid substitutions at no more than 20%, preferably no more than 15% and more preferably no more than 10%, of the residues recited in SEQ ID NO: 16. Variants further include truncated polypeptides and polypeptides containing additional amino acid sequences that have minimal influence on the activity of the polypeptide. A human E3 ubiquitin ligase polypeptide may be of any length, provided that it retains the recited properties. In other words, such a polypeptide may be an oligopeptide (i.e., consisting of a relatively small number of amino acid residues, such as 8-10 residues, joined by peptide bonds), a full length protein (or variant thereof) or a polypeptide of intermediate size (e.g., 20, 50, 200 or 400 amino acid residues).

Certain variants contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, certain E3 polypeptides may contain additional amino acid sequences at the amino and/or carboxy termini. For example, an E3 sequence may be conjugated to a signal (or leader) sequence at the N-terminal end of the protein which co-translationally or post-translationally directs transfer of the protein. A polypeptide may also, or alternatively, be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

The ability of an E3 polypeptide to bind to phosphorylated IκB may be readily determined using any binding assay known to those of ordinary skill in the art. For example, pIκBα/NF-κB complexes may be incubated with immobilized E3 polypeptide, and the level of IκBα binding evaluated using anti-IκBα antibodies (in, for example, a Western blot). Within such assays, an E3 polypeptide should bind detectably to the IκBα; preferably the E3 polypeptide binds at a level that is not substantially diminished relative to the native human E3. In other words, the ability of a variant to bind detectably to phosphorylated and complexed IκBα may be enhanced or unchanged, relative to the native polypeptide, or may be diminished by less than 50%, and preferably less than 20%, relative to the native polypeptide. It will be apparent that other suitable substrates may be substituted for pIκBα/NF-κB complexes within such assays.

The ability of an E3 polypeptide to enhance ubiquitination of phosphorylated IκB may be assessed by incubating the polypeptide with IκBα/NF-κB complex, along with ATPγS, ubiquitin E1 and ubiquitin E2, and detecting the slow-moving IκBα-ubiquitin conjugates by Western blot using IκBα-specific antibodies, as described herein. In general, an E3 polypeptide should result in a detectable level of ubiquitination within such an assay; preferably the level of ubiquitination is not substantially diminished relative to the level of ubiquitination generated by a similar amount of native human E3.

Also encompassed by the present invention are polypeptides comprising a portion or other variant of E3 that retains the ability to bind to phosphorylated IκB, but does not retain the ability to enhance ubiquitination of IκB. Such polypeptides may be readily identified using the binding assays and ubiquitination assays provided herein, and may generally be used to inhibit ubiquitination of IκB. Such polypeptides include those from which the F-box region (i.e., a region of the protein that interacts with one or more components of the ubiquitin cascade) has been deleted. F box regions may generally be identified functionally (i.e., deletion of an F-box region results in a protein that fails to recruit appropriate components of the ubiquitin machinery) and based on the present of an F-box region consensus sequence (see Patton et al., Trends in Genet. 14:236-243, 1998). Certain such polypeptides contain a deletion of amino acids 122-168 of SEQ ID NO:16. Within certain embodiments, portions of E3 may comprise 10 to 374 consecutive amino acid residues, preferably 50 to 250, consecutive amino acid residues of the sequence recited in SEQ ID NO: 16.

The present invention further provides polynucleotides that encode an E3 polypeptide as provided herein. Any polynucleotide that encodes such a polypeptide, or a portion or variant thereof as described herein, is encompassed by the present invention. Such polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Native DNA sequences encoding a human E3, or portion thereof, may be isolated using any of a variety of hybridization or amplification techniques, which are well known to those of ordinary skill in the art. Within such techniques, probes or primers may be designed based on the E3 sequence provided herein, and may be purchased or synthesized. Libraries from any suitable tissue may be screened. An amplified portion or partial cDNA molecule may then be used to isolate a full length gene from a genomic DNA library or from a cDNA library, using well known techniques. Alternatively, a full length gene can be constructed from multiple PCR fragments. Partial and full length polynucleotides comprising such sequences, other portions of full length polynucleotides, and sequences complementary to all or a portion of such full length molecules, are specifically encompassed by the present invention. In addition, homologues from other species are specifically contemplated, and may generally be prepared as described herein.

Polynucleotide variants of the recited sequences may differ from a native E3 polynucleotide in one or more substitutions, deletions, insertions and/or additions. Preferred variants contain nucleotide substitutions, deletions, insertions and/or additions at no more than 20%, preferably at no more than 10%, of the nucleotide positions. Certain variants are substantially homologous to a native gene, or a portion or complement thereof. Such polynucleotide variants are capable of hybridizing under moderately stringent conditions to a naturally occurring DNA sequence encoding an E3 protein (or a complementary sequence). Suitable moderately stringent conditions include prewashing in a solution of 5×SSC, 0.5% SDS, 1.0 mM EDTA (pH 8.0); hybridizing at 50° C.-65° C. 5×SSC. overnight; followed by washing twice at 65° C. for 20 minutes with each of 2×, 0.5× and 0.2×SSC containing 0.1% SDS). Such hybridizing DNA sequences are also within the scope of this invention.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

As noted above, the present invention further provides antisense polynucleotides and portions of any of the above sequences. Such polynucleotides may generally be prepared by any method known in the art including, for example, solid phase phosphoramidite chemical synthesis. Alternatively, RNA molecules may be generated by in vitro or in vivo transcription of DNA sequences that are incorporated into a vector downstream of a suitable RNA polymerase promoter (such as T3, T7 or SP6). Certain portions of a polynucleotide may be used to prepare an encoded polypeptide, as described herein. In addition, or alternatively, a portion may function as a probe (e.g., to detect E3 expression in a sample), and may be labeled by a variety of reporter groups, such as radionuclides, fluorescent dyes and enzymes. Such portions are preferably at least 10 nucleotides in length, and more preferably at least 20 nucleotides in length. Within certain preferred embodiments, a portion for use as a probe comprises a sequence that is unique to an E3 gene. A portion of a sequence complementary to a coding sequence (i.e., an antisense polynucleotide) may also be used as a probe or to modulate gene expression. DNA constructs that can be transcribed into antisense RNA may also be introduced into cells or tissues to facilitate the production of antisense RNA.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Polynucleotides as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Additional initial, terminal and/or intervening DNA sequences that, for example, facilitate construction of readily expressed vectors may also be present. Suitable vectors may be obtained commercially or assembled from the sequences described by methods well-known in the art. Other elements that may be present in a vector will depend upon the desired use, and will be apparent to those of ordinary skill in the art.

Vectors as described herein may generally be transfected into a suitable host cell, such as a mammalian cell, by methods well-known in the art. Such methods include calcium phosphate precipitation, electroporation and microinjection.

E3 polypeptides may generally be prepared using standard automated synthesis techniques or by expression of recombinant DNA encoding the desired polypeptide. In general, peptides may be prepared synthetically using standard techniques, incorporating amino acids and/or amino acid analogs. During synthesis, active groups of amino acids and/or amino acid analogs may be protected as necessary using, for example, a t-butyldicarbonate (t-BOC) group or a fluorenylmethoxy carbonyl (FMOC) group. Amino acids and amino acid analogs may be purchased commercially (e.g., Sigma Chemical Co.; Advanced Chemtec) or synthesized using methods known in the art. Peptides may be synthesized using a solid phase method, in which the peptides are attached to a resin such as 4-methylbenzhydrylamine (MBHA), 4-(oxymethyl)-phenylacetamido methyl- and 4-(hydroxymethyl)phenoxy methyl-copoly(styrene-1% divinylbenzene) (Wang resin), all of which are commercially available, or to p-nitrobenzophenone oxime polymer (oxime resin) which can be synthesized as described by De Grado and Kaiser, *J. Org. Chem.* 47:3258, 1982. Those skilled in the art will realize that the choice of amino acids and/or amino acid analogs will depend, in part, on the specific physical, chemical or biological characteristics desired. Such characteristics are determined, in part, by the method of administration and the target location within a patient.

Selective modification of the reactive groups in a peptide can also impart desirable characteristics. Peptides can be manipulated while still attached to the resin to obtain N-terminal modified compounds such as an acetylated peptide or can be removed from the resin using hydrogen fluoride or an equivalent cleaving agent and then modified. Compounds synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus or amidation of the C-terminus. Similarly, methods for modifying side chains of the amino acids or amino acid analogs are well known to those skilled in the art of peptide synthesis. The choice of modifications made to reactive groups present on the peptide will be determined by the desired characteristics.

An E3 polypeptide may also be a cyclic peptide. A cyclic peptide can be obtained by inducing the formation of a covalent bond between, for example, the amino group at the N-terminus of the peptide and the carboxyl group at the C-terminus. Alternatively, a cyclic peptide can be obtained by forming a covalent bond between a terminal reactive group and a reactive amino acid side chain or between two reactive side chains. It will be apparent to those of skill in the art that a cyclic peptide is selected based on the desired properties. For example, a cyclic peptide may provide increased stability, increased solubility, decreased immunogenicity or decreased clearance in vivo.

A newly synthesized peptide can be purified using a method such as reverse phase high performance liquid chromatography (RP-HPLC) or other methods of separation based on size or charge. Furthermore, a purified peptide can be characterized using these and other well known methods such as amino acid analysis and mass spectrometry.

Alternatively, polypeptides may generally be prepared from nucleic acid encoding the desired polypeptide using well known techniques. To prepare an endogenous protein, an isolated cDNA may be used. To prepare a variant polypeptide, standard mutagenesis techniques, such as oligonucleotide-directed site-specific mutagenesis may be used, and sections of the DNA sequence may be removed to permit preparation of truncated polypeptides.

In general, any of a variety of expression vectors known to those of ordinary skill in the art may be employed to express recombinant polypeptides of this invention. Expression may be achieved in any appropriate host cell that has been transformed or transfected with an expression vector containing a DNA sequence that encodes a recombinant polypeptide. Suitable host cells include prokaryotes, yeast, baculovirus-infected insect cells and animal cells. Following expression, supernatants from host/vector systems which secrete recombinant protein or polypeptide into culture media may be first concentrated using a commercially available filter. Following concentration, the concentrate may be applied to a suitable purification matrix such as an affinity matrix or an ion exchange resin. One or more reverse phase HPLC steps can be employed to further purify a recombinant polypeptide.

In general, polypeptides and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, polypeptides provided herein are isolated to a purity of at least 80% by weight, more preferably to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography. A polynucleotide is considered to be isolated if, for example, it is cloned into a vector that is not a pan of the natural environment.

Antibodies

The present invention further provides antibodies, and antigen-binding fragments thereof, that specifically bind to an E3 polypeptide. As used herein, an antibody, or antigen-binding fragment, is said to "specifically bind" to a polypeptide if it reacts at a detectable level (within, for example, an ELISA) with the polypeptide, and does not react detectably with unrelated proteins. Antibodies may be polyclonal or monoclonal. Preferred antibodies are those antibodies that inhibit or block E3 activity and within a ubiquitination assay as described herein. Other preferred antibodies (which may be used, for example, in immunokinase assays) are those that immunoprecipitate active E3, as determined using any standard assay, such as an assay provided herein.

Antibodies may be prepared by any of a variety of techniques known to those of ordinary skill in the art (see, e.g., Harlow and Lane, *Antibodies: A Laboratory Manual*, Cold Spring Harbor Laboratory, 1988). In one such technique, an immunogen comprising the polypeptide is initially injected into a suitable animal (e.g., mice, rats, rabbits, sheep and goats), preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies may be prepared, for example, using the technique of Kohler and Milstein. *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by, for example, affinity chromatography on protein A bead columns.

Ubiquitination Assays

As noted above, the ability of an E3 polypeptide to modulate ubiquitination of phosphorylated IκB may be assessed by incubating the polypeptide with IκBα/NF-κB complex (or any other suitable substrate), along with ATPγS, ubiquitin E1 and ubiquitin E2, and detecting IκBα-ubiquitin conjugates by, for example, Western blot using IκBα-specific antibodies. IκB polypeptides for use in a ubiquitination assay as described herein may be native human IκBα (SEQ ID NO:1) or IκBβ (SEQ ID NO:3), or may be a variant of a native protein. Polypeptide variants of IκB are generally modified such that the ability of the variant to be phosphorylated and ubiquitinated within a ubiquitination assay as described herein is not substantially diminished. An IκB polypeptide may be labeled. For example, $^{35}$S may be incorporated into a IκB polypeptide by in vitro translation of the polypeptide in the presence of $^{35}$S-methionine, using standard techniques.

An IκB polypeptide may generally be prepared from DNA encoding the polypeptide by expression of the DNA in cultured host cells or by translation using an in vitro system such as wheat germ extract. If host cells are employed, such cells are preferably are bacteria, yeast, baculovirus-infected insect cells or mammalian cells. The recombinant DNA may be cloned into any expression vector suitable for use within the host cell, using techniques well known to those of ordinary skill in the art. In vitro translation of polypeptide may generally be performed according to the manufacturer's instructions.

Expressed IκB polypeptides may be used without purification following in vitro translation. Alternatively, a polypeptide may be isolated in substantially pure form. An IκB polypeptide may be isolated to a purity of at least 80% by weight, preferably to a purity of at least 95% by weight, and more preferably to a purity of at least 99% by weight. In general, such purification may be achieved using, for example, the representative purification method described herein or the standard techniques of ammonium sulfate fractionation. SDS-PAGE electrophoresis, and affinity chromatography.

Certain ubiquitination assays may employ a cellular E3 to characterize modulators of E3 activity. Within such assays, cellular extracts from stimulated or non-stimulated Jurkat, HeLa, THP-1 or endothelial cells may be incubated in vitro with an IκB polypeptide in the presence of ATP and the phosphatase inhibitor okadaic acid. Cellular extracts may generally be prepared according to the method of Alkalay et al., *Proc. Natl. Acad. Sci. USA* 92.10599, 1995. The incubation is performed under conditions sufficient to result in phosphorylation of the IκB polypeptide (at serines 32 and 36 for IκBα and variants thereof) and association of the phosphorylated polypeptide (pIκB) with the cellular-derived NF-κB complex. For example, IκB polypeptide may be incubated with HeLa or Jurkat cell extract, ATP and okadaic acid. Incubation for 90 minutes at 30° C. is generally sufficient to allow phosphorylation of the IκB polypeptide. Following this incubation, the pIκB/NF-κB complex may be immunopurified with, for example, anti-p65 antibodies and subjected to in vitro ubiquitination in a cell free system, as described by Alkalay et al., *Proc. Natl. Acad. Sci. USA* 92:10599, 1995. The level of ubiquitination may then be evaluated using the well known techniques of SDS-PAGE, followed by autoradiography.

Figure 1B:
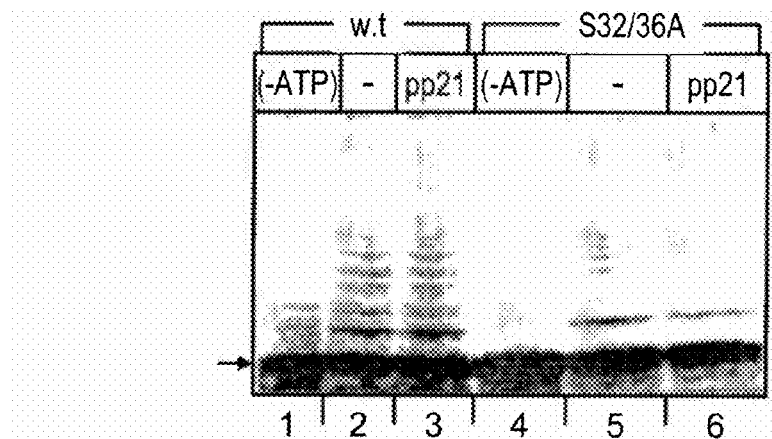

Under these conditions, a wild type $^{35}$S-pIκBα polypeptide generates multiply ubiquitinated species in the presence of ATPγS (see FIG. 1A, lane 4). Neither $^{35}$S-labeled S32/36A mutant of IκBα (lane 1), nor the non-phosphorylated wild type $^{35}$S-IκBα (lane 2) are ubiquitinated. However, free forms of either mutant or wild type IκBα are readily conjugated (FIG. 1B). Similarly, a free (but not a complex-associated) lysine 21, 22 mutant of IκBα can be ubiquitinated in vitro. Thus, unlike ubiquitination assays performed using free IκB polypeptides, the ubiquitination assay provided herein targets only IκB polypeptides that are complex-associated and appropriately phosphorylated.

A ubiquitination assay as described above may be used to identify agents that modulate ubiquitination of IκB. Modulating agents may include antibodies (e.g., monoclonal), peptides, small molecules (e.g., from a combinatorial library) and other drugs that stimulate or, preferably, inhibit ubiquitination of an IκBα and/or IκBβ polypeptide. In general, such agents may be identified by including a candidate modulating agent in the ubiquitination reaction, which may otherwise be performed as described above, and evaluating the effect of the agent on the level of ubiquitination. A suitable concentration of candidate agent for use in such an assay generally ranges from about 0.1 μM to about 1 mM. For peptide candidate agents, a peptidase inhibitor such as Bestatin (40 μg/mL) may also be added, and the amount of peptide preferably ranges from about 10 μM to about 1 mM. A candidate agent that results in a statistically significant effect on the level of ubiquitination is a modulating agent encompassed by the present invention.

Agents may be further evaluated by microinjection of the agent (e.g., about 5 mg/mL of a peptide agent) into a suitable cell (e.g., HeLa cell or primary human vascular endothelial cell). Following microinjection, cells may be stimulated (e.g., with TNFα) and incubated to allow NF-κB activation. In HeLa cells, TNFα induces rapid nuclear translocation n of NF-κB into the nucleus, which may be detected by staining with p65-specific antibodies. Modulating agents induce a statistically significant decrease in NF-κB translocation, and may reduce such translocation to undetectable levels.

Primary human vascular endothelial cells (HUVEC) respond to TNFα stimulation by surface expression of NF-κB regulated adhesion proteins such as ICAM-1, V-CAM-1 and E-selectin (Read et al., *Immunity* 2:493, 1995; Chen et al., *J. Immunol* 155-3538, 1995). E-selectin expression is particularly NF-κB dependent and is the major inducible endothelial adhesion molecule for initial neutrophil attachment and rolling on activated endothelium. Stimulated cells may be fixed and stained to detect expression of one or more NF-κB regulated adhesion proteins. Microinjection of a polypeptide or other modulating agent results in a statistically significant inhibition of such expression, but does not affect the expression of NF-κB independent adhesion proteins, such as ICAM2.

Therapeutic Applications

As noted above, certain E3 polypeptides, polynucleotides, antibodies and other agents as described herein may generally be used as modulating agents to specifically inhibit or enhance cellular NF-κB functions. Modulating agents may also be used to modulate ubiquitination of IκBα and/or IκBβ in a patient, thereby modulating NF-κB cellular function in vivo. As used herein, a "patient" may be any mammal, including a human, and may be afflicted with a disease associated with NF-κB activation, or may be free of detectable disease. Accordingly, the treatment may be of an existing disease or may be prophylactic. Diseases associated with NF-κB activation include, but are not limited to, inflammatory diseases, autoimmune diseases, cancer and viral infection.

Treatment refers to administration of a modulating agent as described herein. For administration to a patient, one or more such compounds are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Alternatively, a pharmaceutical composition may comprise a polynucleotide encoding a modulating agent (such that the modulating agent is generated in situ) in combination with a physiologically acceptable carrier. In such pharmaceutical compositions, the polynucleotide may be present within any of a variety of delivery systems known to those of ordinary skill in the art, including nucleic acid, bacterial and viral expression systems, as well as colloidal dispersion systems, including liposomes. Appropriate nucleic acid expression systems contain the necessary polynucleotide sequences for expression in the patient (such as a suitable promoter and terminating signal). DNA may also be "naked," as described, for example, in Ulmer et al., *Science* 259:1745-1749, 1993.

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific). For example, retroviral vectors can be made target specific by inserting a nucleotide sequence encoding a sugar, a glycolipid, or a protein. Targeting may also be accomplished using an antibody, by methods known to those of ordinary skill in the art.

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) Ψ2, PA317 and PA12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). It has been shown that large unilamellar vesicles (LUV), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques* 6:882, 1988).

The targeting of liposomes can be classified based on anatomical and mechanistic factors. Anatomical classification is based on the level of selectivity and may be, for example, organ-specific, cell-specific, and/or organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Routes and frequency of administration, as well doses, will vary from patient to patient. In general, the pharmaceutical compositions may be administered intravenously, intraperitoneally, intramuscularly, subcutaneously, intracavity or transdermally. Between 1 and 6 doses may be administered daily. A suitable dose is an amount that is sufficient to show improvement in the symptoms of a patient afflicted with a disease associated with NF-κB activation. Such improvement may be detected by monitoring inflammatory responses (e.g., edema, transplant rejection, hypersensitivity) or through an improvement in clinical symptoms associated with the disease. In general, the amount of modulating agent present in a dose, or produced in situ by DNA present in a dose, ranges from about 1 μg to about 100 mg per kg of host. Suitable dose sizes will vary with the size of the patient, but will typically range from about 10 mL to about 500 mL for 10-60 kg animal.

The following Examples are offered by way of illustration and not by way of limitation.

EXAMPLES

Example 1

Identification of an IκB E3 Recognition Motif Using Ubiquitination Assay

This Example illustrates a representative ubiquitination assay, and the use of such an assay to evaluate peptides for the ability to inhibit IκB ubiquitination.

A. In Vitro Ubiquitination Assay

HA-tagged IκBα or HA-tagged IκBβ cDNAs (Haskill et al., *Cell* 65:1281-1289, 1991) were translated in vitro in wheat germ extract in the presence of $^{33}$S-methionine according to the manufacturer's instructions (Promega, Madison, Wis.). To phosphorylate IκBα or IκBβ, 1 μl of the extract containing the labeled protein was incubated for 90 minutes at 30° C. in a reaction mixture having a final volume of 30 μl: 100 μg HeLa or Jurkat cell extract (prepared as described by Alkalay et al., *Proc. Natl. Acad. Sci. USA* 92:10599, 1995), 2 mM ATP and 1 μM okadaic acid. During this incubation, the labeled IκB polypeptide was phosphorylated at serines 32 and 36, and associated with the endogenous NF-κB complex (data not shown).

Following incubation, 1 μl of anti-p65 serum was added, and the NF-κB immune complex was immobilized to Protein A-Sepharose® and subjected to in vitro ubiquitination in HeLa cell extract as described by Alkalay et al. Ubiquitinated proteins were separated by SDS-PAGE and visualized by autoradiography.

As shown in FIG. 1A, only wild type $^{35}$S-pIκBα generated multiply ubiquitinated species (lane 4). Neither $^{35}$S-labeled S32/36A mutant of IκBα (lane 1) nor the non-phosphorylated wild type $^{35}$S-IκBα (lane 2) were ubiquitinated, and no ubiquitination of pIκBα was seen in the absence of ATP (lane 3).

The physiological relevance of this assay was further documented by comparison of in vitro ubiquitination of free $^{35}$S-IκB to that of a complex-associated, phosphorylated substrate. Whereas a complex-associated S32/36A mutant was not subject to ubiquitin conjugation in accordance with its in vivo fate, free forms of either mutant or wild type IκBα were readily conjugated (FIG. 1B). Similarly, only free, but not a complex-associated lysine 21, 22 mutant of IκBα could be ubiquitinated in vitro (data not shown). Thus, while the free IκBα is recognized by the ubiquitin system in a non-discriminatory manner, the complex-associated inhibitor is masked unless it is appropriately phosphorylated.

B. Identification of the IκBα-Ubiquitin Ligase Recognition Motif

To identify the IκBα-ubiquitin ligase recognition motif, various peptides were added at varying concentrations to the reaction mixtures in the presence of the peptidase inhibitor Bestatin (40 μg/ml). The peptides spanned the N-terminal signaling domain of the protein, and were phosphorylated at one or both serine residues (32 and 36), or were unmodified or serine-substituted. These peptides were included in the ubiquitination reaction at different concentrations and tested for inhibition of pIκBα specific ubiquitination. When conjugation of free IκBα was monitored, the translated protein was added directly to the conjugation reaction mixture.

Only peptides that were phosphorylated at both serine 32 and 36 (pIκBα peptides) effectively inhibited pκBα ubiquitination (FIG. 1A, lanes 7, 11-14). A c-Fos phosphopeptide (ppFos, lane 5), a serine 32, 36 to alanine substituted IκBα peptide (p21 S/A, lane 6) and a non-phosphorylated peptide (p21, lane 8) had no detectable effect on the ubiquitination of pIκB at a concentration of 400 μM. The $IC_{50}$ of the phosphorylated IκBα peptides were calculated and representative inhibitory concentrations are shown in FIG. 1A. Doubly phosphorylated IκBα peptides inhibited the pIκB conjugation reaction (lanes 7, 11-14) at an $IC_{50}$ of 5 μM. The sequences of these peptides are provided in Table I, above, and in SEQ ID NOs:5-9. In contrast, singly phosphorylated peptides (lanes 9, 10) inhibited the pIκBα conjugation at an $IC_{50}$ of 400 μM. The minimal size peptide tested (pp7, lane 14), merely spanning the signaling phosphorylation site, was sufficient to effectively inhibit the ubiquitination, although at somewhat higher $IC_{50}$ (10 μM). Thus, a peptide comprising residues 21 to 41 of SEQ ID NO:1 comprises a recognition domain for E3 ubiquitin ligase. Interestingly, lysine residues 21 and 22 are not essential for inhibition, implying that the ubiquitin-system recognition site is distinct from the actual conjugation site.

Figure 1C:
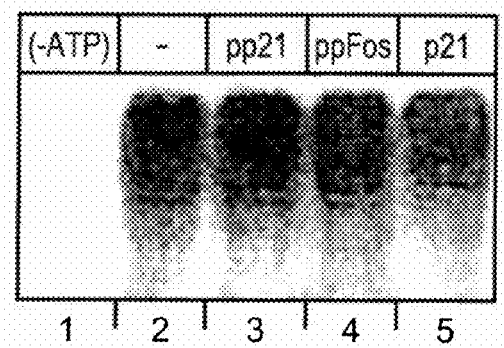

The specificity of the peptides was tested in two other ubiquitin-conjugation reactions: the conjugation of free wild type (FIG. 1B lanes 1-3) or S32/36A mutant IκBα (FIG. 1B, lanes 4-6) and the ubiquitin conjugation to the bulk of cellular proteins in HeLa extract (detected by $^{125}$I-labeled ubiquitin according to Alkalay et al., FIG. 1C). Neither reaction was affected by the addition of an IκBα-ubiquitin ligase recognition motif or a control peptide.

Figure 1D:
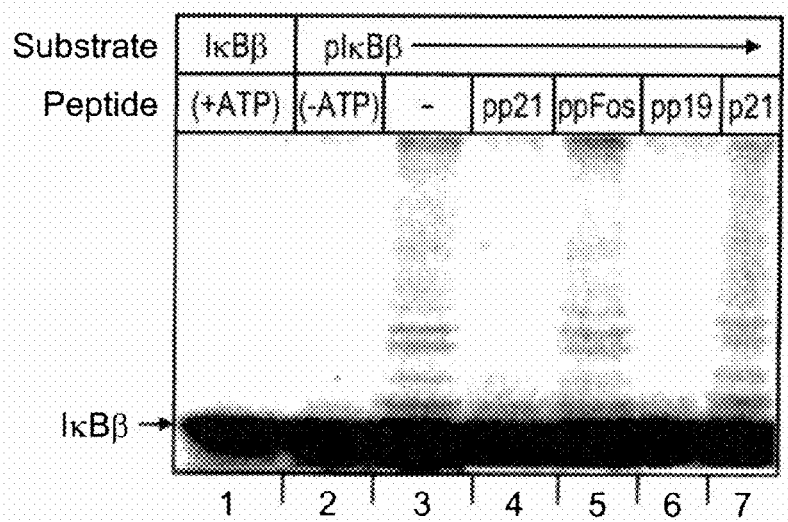

Peptides comprising an IκBα-ubiquitin ligase recognition motif were found to abolish the ubiquitination of the pIκBα related substrate pIκBβ (FIG. 1D). Similar to the conjugation of pIκBα, the specific conjugation of the IκBβ also required an associated NF-κB complex (not shown) and prior phosphorylation at the IκBα-homologous residues Ser 19 and 23. An IκBβ substrate prepared in the absence of phosphatase inhibitors was not subject to ubiquitination (FIG. 1D, lane 1). Peptides affected pIκBβ ubiquitination at an $IC_{50}$ that was similar to that observed for pIκBα (FIG. 1D, lanes 4-7). Hence, it appears that the same enzyme(s) target both IκBs for ubiquitin-dependent degradation.

Figure 2:
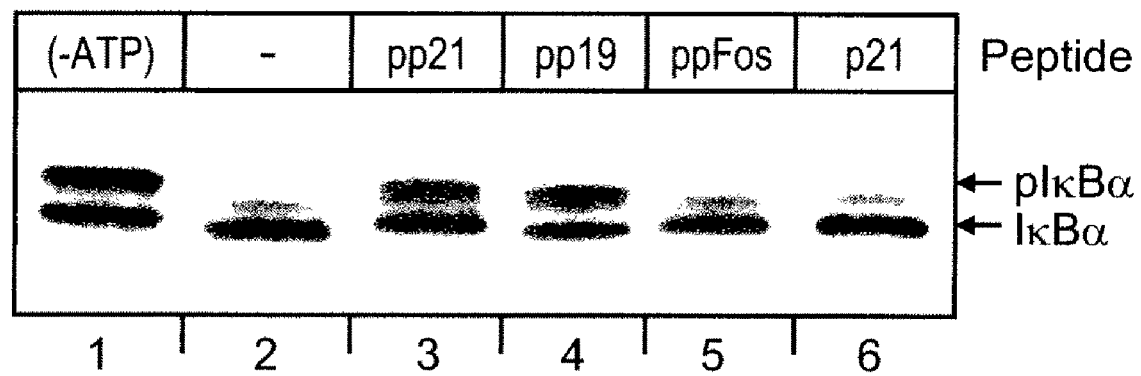
FIG. 2 is an autoradiogram depicting the results of an in vitro ubiquitin-dependent degradation assay performed using extracts from stimulated HeLa cells. In each lane of the SDS-PAGE, the level of phosphorylated (upper band) and non-phosphorylated (lower band) HA-tagged IκBα polypeptide (SEQ ID NO: 12) following the degradation assay is shown. Lane 1 shows the level of these polypeptides following a degradation assay performed without ATP. In lanes 2-6, ATP was included in the reaction mixture. 40 μM candidate modulating agents were added to the reactions shown in lanes 3-6: doubly phosphorylated IκBα peptide (pp21 (SEQ ID NO:9), lane 3); doubly phosphorylated IκBα peptide (pp19 (SEQ ID NO:8), lane 4); c-Fos phosphopeptide (ppFos (SEQ ID NO: 10), lane 5); and non-phosphorylated IκBα peptide (p21 (SEQ ID NO:9), lane 6).

The inhibitory pIκBα peptides were tested in a complementary ubiquitin-dependent in vitro degradation assay (Orian et al., *J. Biol. Chem.* 270:21707, 1995; Stancovski et al., *Mol. Cell. Biol.* 75:7106, 1995). Using this assay, only pIκBα derived from stimulated cells is degraded in vitro in a ubiquitin-dependent manner, whereas the non-phosphorylated IκBα from the same cell extract is not subject to degradation. Incorporation of the conjugation-inhibitory phosphopeptides into the degradation assay resulted in stabilization of the pIκBα substrate (FIG. 2, lanes 3, 4) whereas the non-phosphorylated peptide agent or a control phospho-Fos peptide had no effect on the specific pIκBα degradation (lanes 5, 6). Trimming the peptides at Lys 21/22 did not diminish the degradation inhibitory effect (lane 4), indicating that the peptides do not abolish pIκBα degradation by exhausting the ubiquitin-proteasome system as conjugatable substrates.

Example 2

Identification of Ubiquitin System Component Involved in Substrate Recognition

This Example illustrates the identification of a specific E3 that is responsible for recognition of pIκB polypeptides.

pIκBα-ubiquitin conjugation and degradation requires a full complement of the ubiquitin system enzymes: E1, a specific E2 derived from the ubiquitin system fraction I, E2F1 (Alkalay et al., *Proc. Natl. Acad. Sci. USA* 92:10599, 1995; Chen et al., *Cell* 84:853, 1996) and a Fraction II-component E3. To identify the ubiquitin system component involved in the substrate recognition, HeLa lysate was fractionated over IκBα phosphopeptide columns, and the flow-through fractions were assayed for pIκBα conjugation. Peptides were coupled to NHS-Sepharose® (Pharmacia) according to the manufacturer's instructions at a concentration of 2 mg/ml. 100 μg of HeLa extract were incubated with 2.5 μl coupled resin in the presence of 0.1% NP40 and 3% ovalbumin for 1 hour at 4° C. The resin was discarded and the unbound material tested in the ubiquitination assay described above.

Figure 3A:
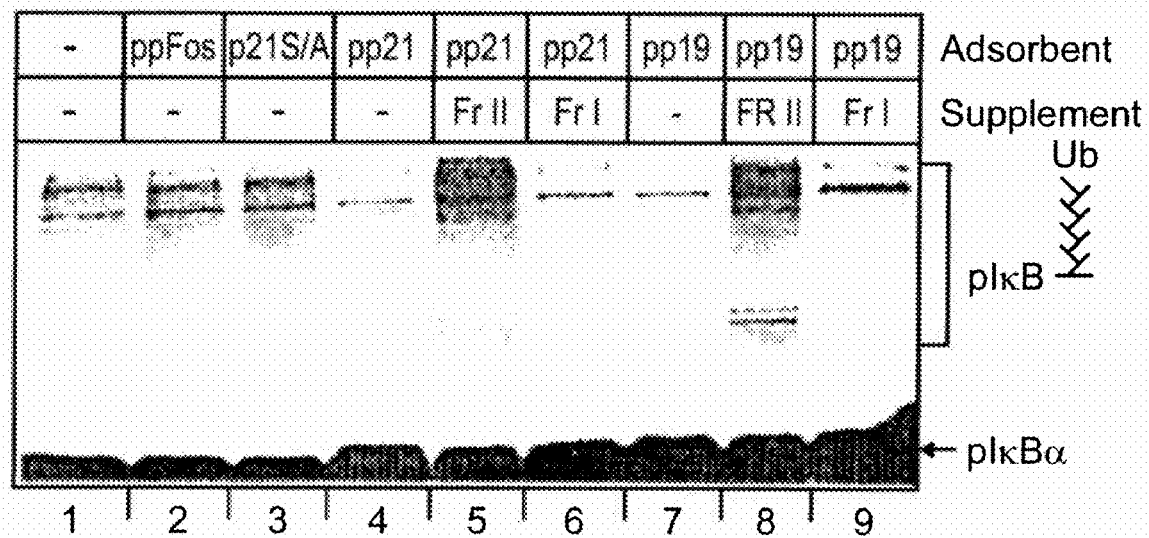
FIG. 3A is an autoradiogram depicting the results of SDS-PAGE analysis of ubiquitination assays performed using flow-through fractions of HeLa cell lysate fractionated over modulating agent columns. In each case, the substrate was a $^{35}$S-labeled, HA-tagged IκBα polypeptide (SEQ ID NO:12) that was phosphorylated and NF-κB complex-associated. Lane 1 shows the level of ubiquitination using a non-fractionated extract. In lanes 2-9, the extract was fractionated over a peptide-Sepharose® column. The peptides used were: c-Fos phosphopeptide (ppFos (SEQ ID NO: 10), lane 2); serine 32, 36 to alanine substituted IκBα peptide (pp21S/A (SEQ ID NO:11), lane 3); doubly phosphorylated IκBα peptide (pp21 (SEQ ID NO:9), lanes 4-6); and doubly phosphorylated IκBα peptide (pp19 (SEQ ID NO:8), lanes 7-9). In addition, reticulocyte Fraction II (160 μg) was added to the ubiquitination reactions shown in lanes 5 and 8, and Fraction I (160 µg) was added to the reactions in lanes 6 and 9.
Figure 3B:
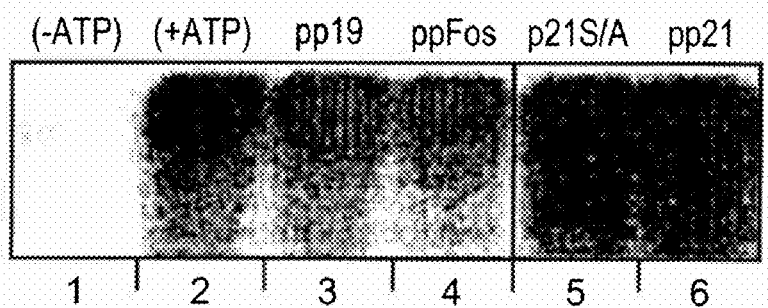
FIG. 3B is an autoradiogram showing the ubiquitination of bulk cellular proteins in HeLa extract. Lane 1 shows the ubiquitination in the absence of ATP, and lane 2 shows the ubiquitination in the presence of ATP, but without candidate modulating agent. In lanes 3-6, candidate modulating agents were added: 40 µM doubly phosphorylated IκBα peptide (pp19 (SEQ ID NO:8), lane 3); 400 µM c-Fos phosphopeptide (ppFos (SEQ ID NO: 10), lane 4); 400 µM serine 32, 36 to alanine substituted IκBα peptide (pp21 S/A (SEQ ID NO:11), lane 5); and 40 µM doubly phosphorylated IκBα peptide (pp21 (SEQ ID NO:9), lane 6).

Whereas a flow-through fraction from a control phosphopeptide column and an S32/36A peptide column retained full IκBα conjugation capacity (FIG. 3A. lanes 2, 3) flow-through fractions from two different pIκBα peptides lost their IκBα specific conjugation capacity (lanes 4, 7). The depleted conjugating activity could be complemented by reticulocyte Fraction II (lanes 5, 8) that contains all the known species of E3 enzymes (Ciechanover, *Cell* 79:13, 1994). Complementation could not be obtained by the addition of Fraction I or Fraction I and E1 (lanes 6 and 9, respectively), indicating that the peptide columns depleted an E3 rather than E2 or E1. Again. IκBα lysine residues 21 and 22 were dispensable for retaining the E3 (compare FIG. 3A, lane 7 to lane 4), emphasizing the distinction between the substrate recognition and conjugation site. The peptide column depletion was found to be specific for the IκB E3, as all flow-through fractions maintained full activity in random HeLa protein conjugation (as detected by measuring the conjugation of $^{125}$I ubiquitin, FIG. 3B). This indicates that a specific E3 is responsible for recognition of the pIκBs at the identified motif.

Example 3

Effect of Representative Peptides on Cellular NF-κB Activation

This Example illustrates the inhibition of cellular NF-κB activation by microinjection of peptides comprising an IκBα-ubiquitin ligase recognition motif.

HeLa cells were plated on a grid coverslips (Cellocate, Eppendorf) 18 hours before microinjection. Microinjection was performed with a 22 amino acid pIκBα peptide (pp21; Table I and SEQ ID NO:9) or a control phospho-Fos peptide (SEQ ID NO: 10) using a semi-automated apparatus (Eppendorf). Peptides were injected into the cell cytoplasm at a concentration of 5 mg/ml in 100 mM KCl, 5 mM Na$_2$HPO$_4$ (pH 7.2), and immediately activated with TNFα (200 units/mL) for either 20 minutes (for NF-κB translocation) or 3 hours (for E-selectin expression). Following activation, the cells were fixed and stained with p65 specific antibodies (Mercurio et al., *Genes & Dev.* 7:705, 1993; Santa Cruz) or monoclonal anti-E-selectin antibodies (R&D Systems).

Figure 4D:
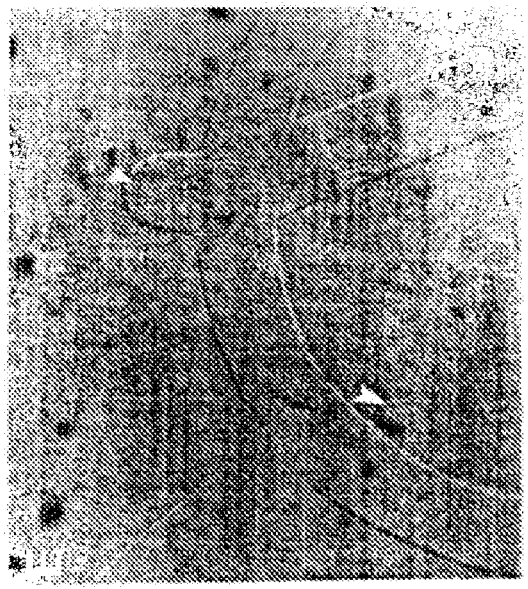
Figure 4E:
Figure 4F:
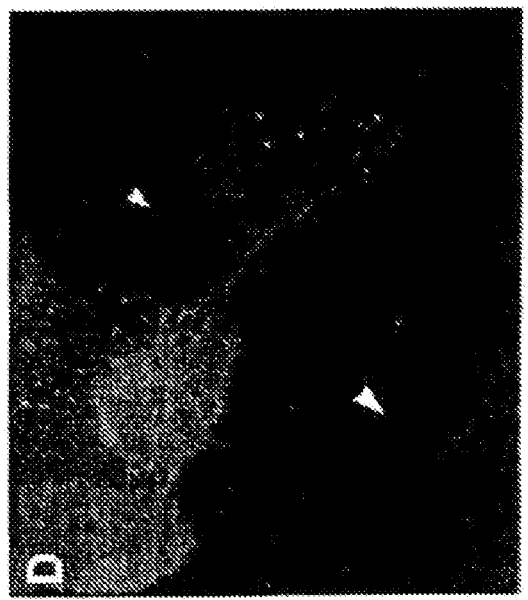
Figures 4G, 4H:
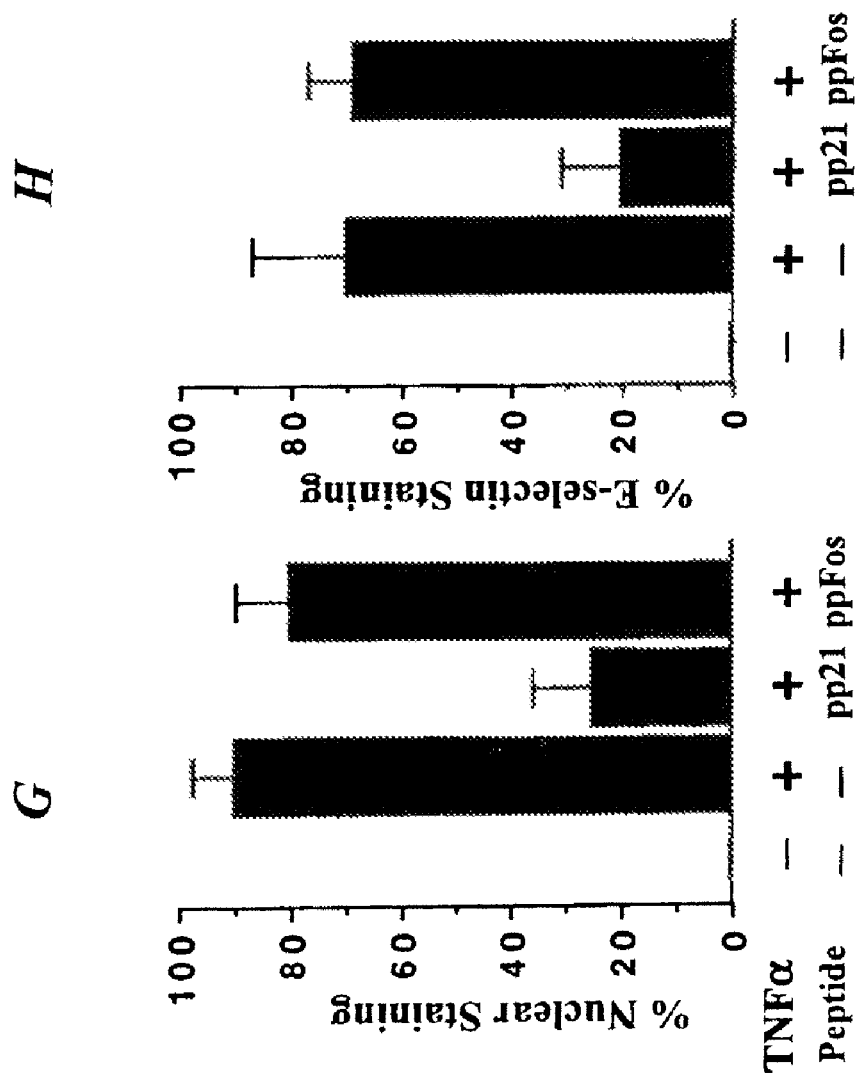
FIGS. 4G and 4H are graphs presenting a summary of the microinjection experiments shown in FIGS. 4A-4F.

In the absence of peptide. TNFα induces rapid nuclear translocation of NF-κB into the nucleus, as shown by the p65 nuclear staining of 90% of the cells (see FIG. 4G, column 2). The pp21 peptide abolished TNFα-stimulated NF-κB activation in 50%-70% of the microinjected cells in several experiments (see representative fields in FIGS. 4A and 4B; and FIG. 4G, column 3). In contrast, the control pp-Fos peptide had no effect on the rate of NF-κB induced nuclear translocation, as compared to non-microinjected cells (FIGS. 4C and 4G, column 4).

To further assess the functional consequences of NF-κB inhibition, the IκB-E3 inhibitory peptide was microinjected into primary human vascular endothelial cells (HUVEC; Chen et al, *J. Immunol* 155:3538, 1995). These cells respond to TNFα stimulation by surface expression of NF-κB regulated adhesion proteins, such as E-selection. HUVEC cells were plated, microinjected and stimulated as described above. Three hours post stimulation the cells were fixed and stained for expression of the NF-κB dependent E-selection. 75%-85% of the HUVEC cells were intensely stained for E-selectin following TNFα stimulation in several experiments. Microinjection of the pp21 peptide resulted in the inhibition of E-selectin expression in 70%-80% of the microinjected cells (FIG. 4D; and FIG. 4H, column 3). In contrast, the control pp-Fos peptide had no effect on E-selectin expression, as compared to non-microinjected cells (FIGS. 4F and 4H, column 4). Microinjection of a control, S32736A substituted IκBα peptide had no effect on the rate of E-selectin expression.

These results demonstrate that the subunit-specific degradation of the signal-induced phosphorylated IκBα and IκBβ is mediated by a specific E3. The recognition domain for E3 ubiquitin ligase is a short sequence, centered around the two signal-acquired phosphoserines conserved in both IκBs, representing the first biologically relevant E3 recognition motif. The specificity in IκB recognition is supported by the context of the phosphorylated substrate: an associated cellular complex masks the substrate from non-specific E3s. This feature restricts the NF-κB inhibitor degradation to the post-stimulation phase, at which it is exposed through site-specific phosphorylation event(s) to the specific ligase. NF-κB activation and its resultant function can be specifically abolished by in vivo inhibition of the IκB ligase, using a modulating agent as provided herein.

Example 4

Further Characterization of IκBα Ubiquitination

This Example further illustrates the characterization of the ubiquitin ligase associated with IκBα ubiquitination.

A. Cytokine Stimulation Promotes the Association Between pIκBα and a Specific Ubiquitin-Ligase To further study the recruitment of components of the ubiquitin machinery by phosphorylated IκBα-complexes, pIκBα/NF-κB complexes were purified from proteasome inhibited, TNF-α stimulated HeLa cells, and their ubiquitination potential was evaluated. HeLa cells were pre-incubated with the proteasome inhibitor ALLN (150 μM) for 1 hour and stimulated for 10 minutes with TNFα. IκBα/NF-κB complexes were immunoaffinity-purified with goat anti-Rel A (p65) antibodies (Santa Cruz Biotechnology, Inc., Santa Cruz, Calif.) and the cognate p65 peptide (ELFPLIF-PAEPAQASGP (SEQ ID NO:21), which was synthetic and purchased from Alfa-Diagnostic, Inc., and then HPLC-purified, analyzed by mass spectrometry, verified for the predicted structure and proven to be over 85% pure).

The immunopurified fraction was supplemented with various components of the ubiquitin system and subjected to in vitro ubiquitination. In particular, the fraction was supplemented with 0.2 µg purified E1 and 1 µg purified recombinant UBC5C (Jensen et al., J. Biol. Chem. 270:30408-30414, 1995) and incubated for 90 minutes at 37° C. in reaction buffer containing: 50 mM Tris (pH 7.6), 2 mM MgCl$_2$, 1 mM DTT, 20 nM okadaic acid, 1 mg/ml bovine ubiquitin (Sigma) and 5 mM ATPγS (Sigma). The reaction mix was then boiled in SDS-buffer and the sample analyzed by SDS-PAGE (8.5%) and phospho-imaging.

Figure 5:
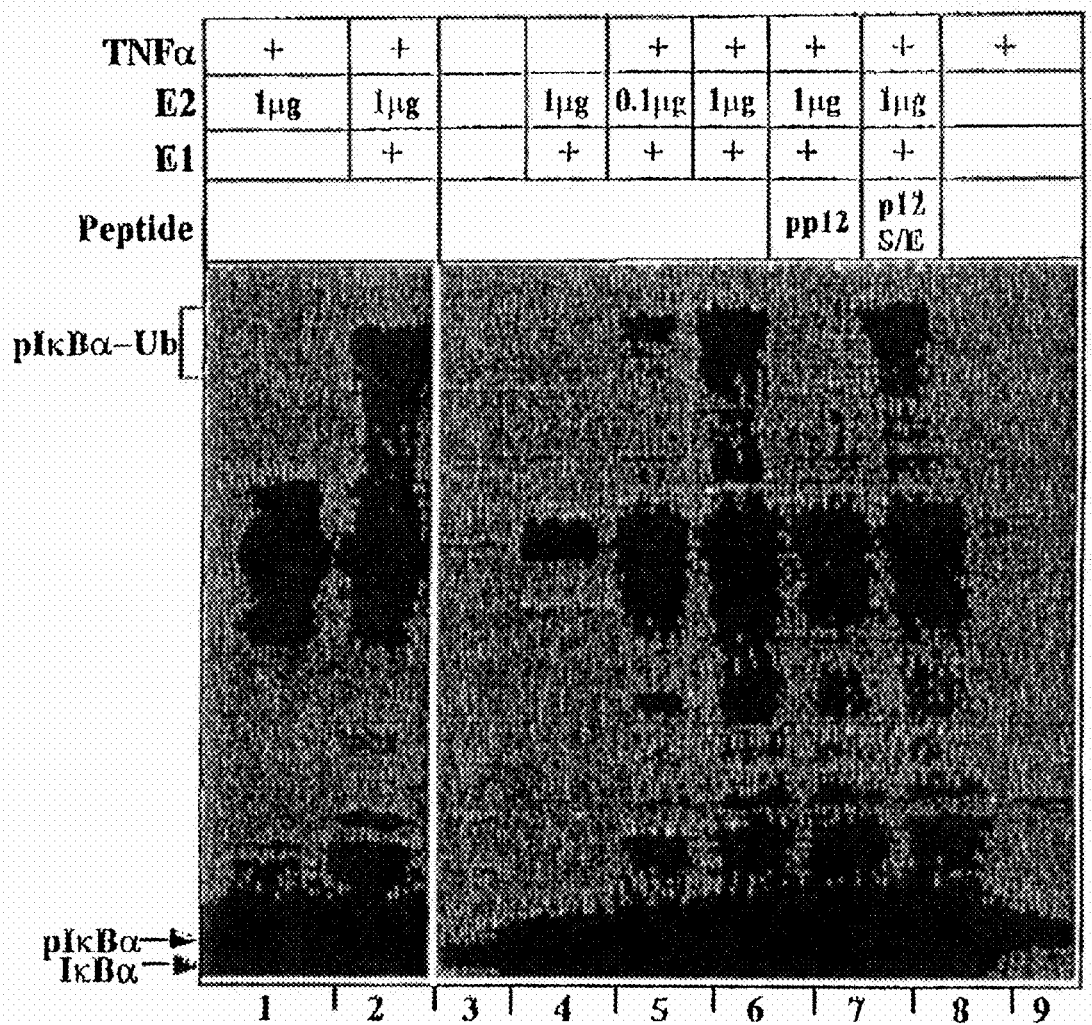
FIG. 5 is an autoradiogram depicting the results of a Western blot analysis showing the immunoprecipitation of pIκBα-associated ubiquitin-ligase activity from TNFα-activated cells. The pIκBα/NF-κB complex was immunoprecipitated from proteasome-inhibited, TNFα-stimulated or non-stimulated HeLa cells and subjected to in vitro ubiquitination upon addition of ubiquitin, ATP-γS and the following components: lane 1, UBC5C; lane 2. UBC5C and E1; lane 3, none; lanes 4-6, UBC5C and E1 as indicated; lane 7. UBC5C, E1 and pIκBα-peptide; lane 8, UBC5C, E1 and serine-substituted IκBα peptide; lane 9, a sample of TNFα-stimulated HeLa lysate. Cell-stimulation is indicated in the TNFα row. Monomeric and ubiquitin-conjugated IκBα are marked at the left, bottom and top of the figure.

The addition of ubiquitin, purified E1 and a specific E2, UBC5C, was found to be sufficient to generate the full capacity IκBα-ubiquitin conjugating activity (FIG. 5, lane 2), evident in the accumulation of high-molecular mass species that reacted with IκBα specific antisera. This activity was E1-dependent (compare lanes 1 and 2), and was not provided by the corresponding immunopurified fraction from non-stimulated HeLa cells (compare lanes 4, 5, 6). As the stimulated HeLa fraction contained both phosphorylated and non-phosphorylated IκBα, the observed conjugates could be derived from either IκB species.

To determine the source of the IκBα-conjugates, the ubiquitination reactions were performed in the presence of a pIκBα peptide (pp12; CDRHDS[PO3]GLDS[PO3]; SEQ ID NO:22) (lane 7) or a serine/glutamic-acid substituted IκBα peptide (p12S/E) (lane 8). Both peptides were synthetic, purchased from Alfa-Diagnostic, Inc., and then HPLC-purified, analyzed by mass spectrometry, verified for the predicted structure and proven to be over 85% pure. IκBα peptides were added at the indicated concentrations to the reaction mixtures in the presence of the peptidase inhibitor Bestatin (40 µg/ml). Only pp12 abolished the formation of polyubiquitin-IκBα conjugates, indicating that ubiquitination was specific for pIκBα (Yaron et al., EMBO J. 76:6486-6494, 1997).

B. Phosphorylation is Necessary and Sufficient to Recruit Specific Ubiquitin-Ligase Activity The finding that E1 and E2 specifically complemented pIκBα-conjugation of the stimulated HeLa fraction, but failed to complement a non-stimulated fraction, could be explained in several ways: a) HeLa stimulation activates a specific pIκB-ubiquitin ligase, b) HeLa stimulation modifies the substrate, thus rendering it liable to ubiquitination, or c) HeLa stimulation is necessary for modifying both the substrate and the ligase. To distinguish among these possibilities, a recombinant, constitutively active IKK2 protein (IKK2-EE) was used (Mercurio et al., Science 278:860-66, 1997). This protein phosphorylates IκBα at serine 32/36 similarly to a TNFα activated IKK-complex.

Figure 6:
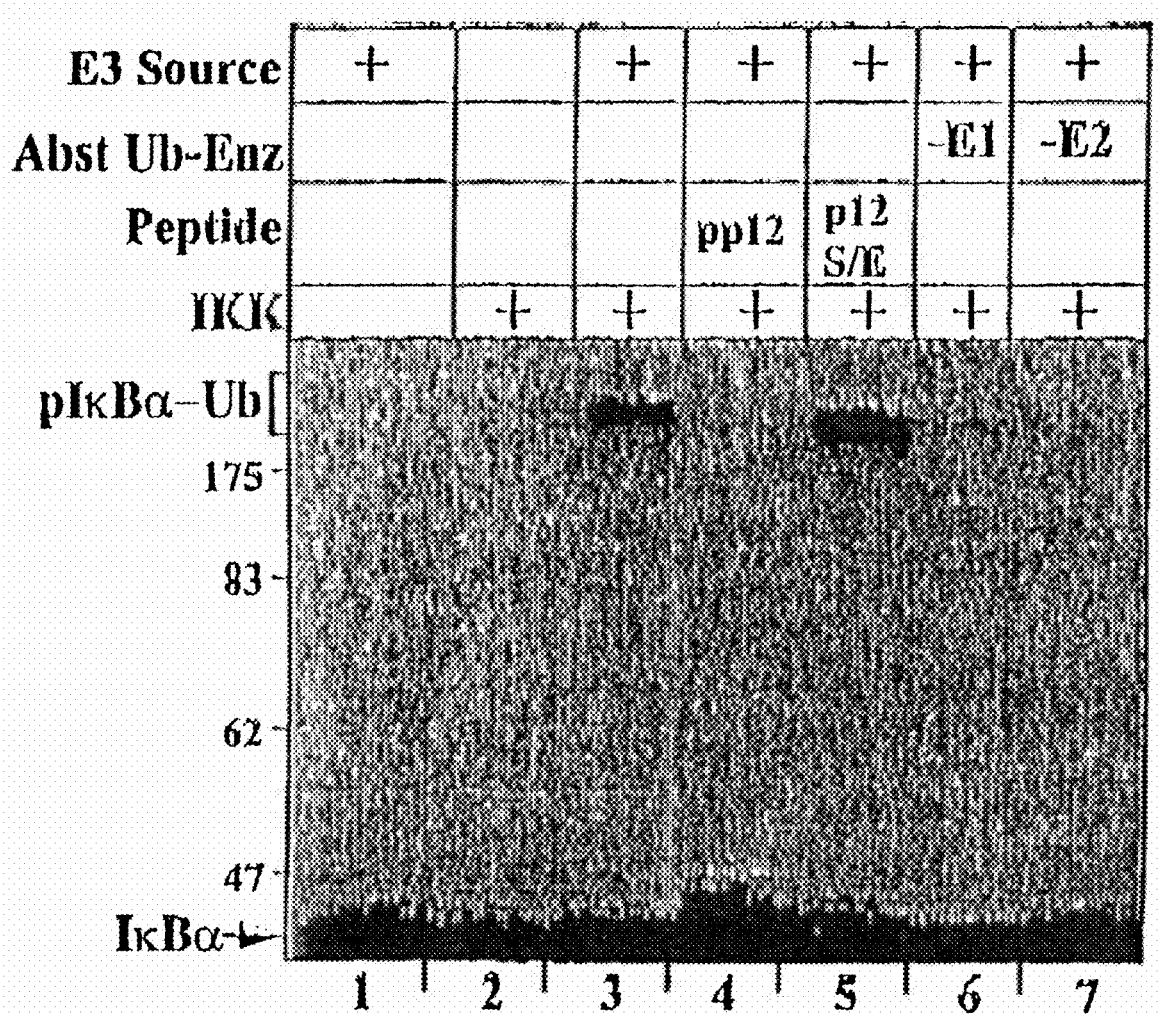
FIG. 6 is an autoradiogram illustrating the association of the ubiquitin-ligase with the IκBα/NF-κB complex, following IKK-phosphorylation of IκBα at the DSGLDS (SEQ ID NOs:8 and 19) site. $^{35}$S-labeled IκBα/NF-κB complex immunopurified from non-activated cells was phosphorylated by IKK-2EE (where marked by — at the top), incubated with non-activated HeLa lysate as an E3 source, washed and subjected to in vitro ubiquitination in the presence of ATPγS, ubiquitin, E1, UBC5C (except where an excluded component is indicated by Abst Ub-Enz). Lanes 2-7 show phosphorylation by IKK: lanes 1 and 3-7 show the effect of incubation with HeLa lysate; in lane 4, a pκBα peptide was added during the incubation with HeLa lysate; in lane 5, serine-substituted IκBα peptide was added during HeLa incubation; in lane 6, E1 was omitted from the ubiquitination stage; and in lane 7, UBC5C was omitted during ubiquitination.

Following immunoprecipitation of $^{35}$S-labeled IκBα/NF-κB complexes from a non-stimulated HeLa lysate previously incubated with recombinant $^{35}$S-labeled IκBα, the complexes were phosphorylated by the recombinant IKK2-EE, eluted with the p65 cognate peptide and subjected to in vitro ubiquitination. After incubation with IKK2-EE, nearly all of the $^{35}$S-IκB was phosphorylated. Yet, the addition of ubiquitin, E1 and UBC5C did not result in pIκBα phosphorylation (FIG. 6, lane 2). Therefore, IκB phosphorylation by IKK was not sufficient to promote its ubiquitination in the presence of E1 and E2. Conceivably, pIκBα ubiquitination requires an additional component of the HeLa lysate that was not co-immunopurified from non-stimulated cells.

To confirm this hypothesis, immuno-bound IκBα/NF-κB complexes were incubated with a non-stimulated HeLa lysate, either directly or following IKK2-EE phosphorylation, washed extensively with high-salt buffer and eluted with the p65 peptide. Indeed, incubation of the phosphorylated IκB complexes (FIG. 6 lane 3), but not of the non-phosphorylated ones (lane 1), with the HeLa lysate, provided the pIκB-ligase component(s) necessary for pIκBα conjugation. No signal was obtained when E1 or E2 were omitted from the reaction, confirming that the signal at the top of the gel represents poly-ubiquitin IκBα-conjugates (lanes 5, 6). TNFα stimulated HeLa-lysate was not superior over a non-stimulated lysate in providing the necessary ligase component.

The inhibitory effect of pp12 on pIκBα-ubiquitination (FIG. 5) suggested that the essential HeLa component associates specifically and stably with the pIκBα recognition motif during the incubation period and later functions in pIκB-ubiquitin conjugation. To test this assumption, we included in the incubation step pp12 or the control peptide p12S/E, which was removed together with the HeLa lysate, before eluting the fractions. The addition of pp12 (FIG. 6, lane 4), but not of p12S/E (lane 5), abrogated the ubiquitin-ligase activity associated with the pIκB-complex, while preserving the integrity of the substrate. This was evident in the ability of the peptide-treated fractions to undergo ubiquitination in the presence of Reticulocyte Fraction II as an E3 source (Alkalay et al., Mol. Cell Biol. 15:1294-301, 1995). Several conclusions may be drawn from this experiment:

1) A ubiquitin-ligase component essential to pIκBα ubiquitination is recruited by the IκBα/NF-κB complex from the HeLa lysate following IKK phosphorylation.

2) This conjugation-promoting component is contained in a non-stimulated HeLa lysate, indicating that there is no need to activate the ubiquitin-ligase by TNF-stimulation.

3) The essential ligase component is apparently specific and associates with IκB through a direct interaction with the pIκB recognition motif (proved by pp12 inhibition of pIκBα-conjugation).

C. Isolation of the Specific Ubiquitin-Ligase Component that Recognizes pIκBα

HeLa extract (250 mg) was incubated with 250 µl anti-p65 immunobeads. Following four washes in buffer A (1M KCl, 0.5% NP40, 50 mM Tris buffer pH 7.6, 1 mM DTT) and one wash in buffer B (50 mM Tris buffer, pH 7.6, 1 mM DTT), half the beads were subject to in vitro phosphorylation with IKK and half underwent mock-phosphorylation. The beads were washed twice in buffer A and once in buffer B, agitated with 100 mg HeLa extract in the presence of 1 µm okadaic acid for 30 min at 25° C., washed four times with buffer A, once in buffer A and eluted with 1 mg/ml p65 peptide. A similar experiment was performed with 10 mg $^{35}$S-metabolically-labeled HeLa cell lysate (100 µCi/ml Met/Cys for 8 hours) and 25 µl p65-immunobeads. Eluate-fractions derived from both the hot and cold lysates were mixed, boiled in SDS-sample buffer and analyzed by 7.5% SDS-PAGE and autoradiography. Gel slices corresponding to the autoradiogram signals were excised and their protein-bands sequenced by mass-spectrometry, as described below.

Three immunoaffinity-purified fractions were compared by SDS-page analysis (FIG. 7A): 1) a fraction containing IκBα/NF-κB complexes that was not phosphorylated by IKK2-EE, but incubated with HeLa lysate; 2) a fraction subjected to IKK2-EE phosphorylation and subsequent incubation with HeLa lysate; 3) a fraction phosphorylated by IKK2-EE, but not incubated with HeLa lysate. All incubations were performed on immunobead-immobilized complexes, which were then extensively-washed and eluted with the p65 peptide.

SDS-PAGE analysis of the three fractions revealed pattern-changes due to IKK phosphorylation or to further immuno-adsorption of IκBα/NF-κB proteins, but did not discern any protein recruited to the IκB-complex following IKK phosphorylation. The complexity of the protein staining could obscure the presence of any recruited protein migrating along with an immunopurified protein. To identify the recruited protein, mass-spectrometry analysis was performed on a dozen Colloidal Blue-stained bands derived from fractions 1 and 2. This analysis revealed the presence of nearly the full spectrum of the Rel family proteins and IκBα: NF-κB1 (p105), NF-κB2 (p100). RelA (p65). p50, p49. C-Rel. IκBα and IκBε. Only a few other proteins were co-immunoprecipitated with the IκB/NF-κB complex, particularly GRP78/Bip, Hsp 70 and Hsc 70.

Figures 7A, 7B:
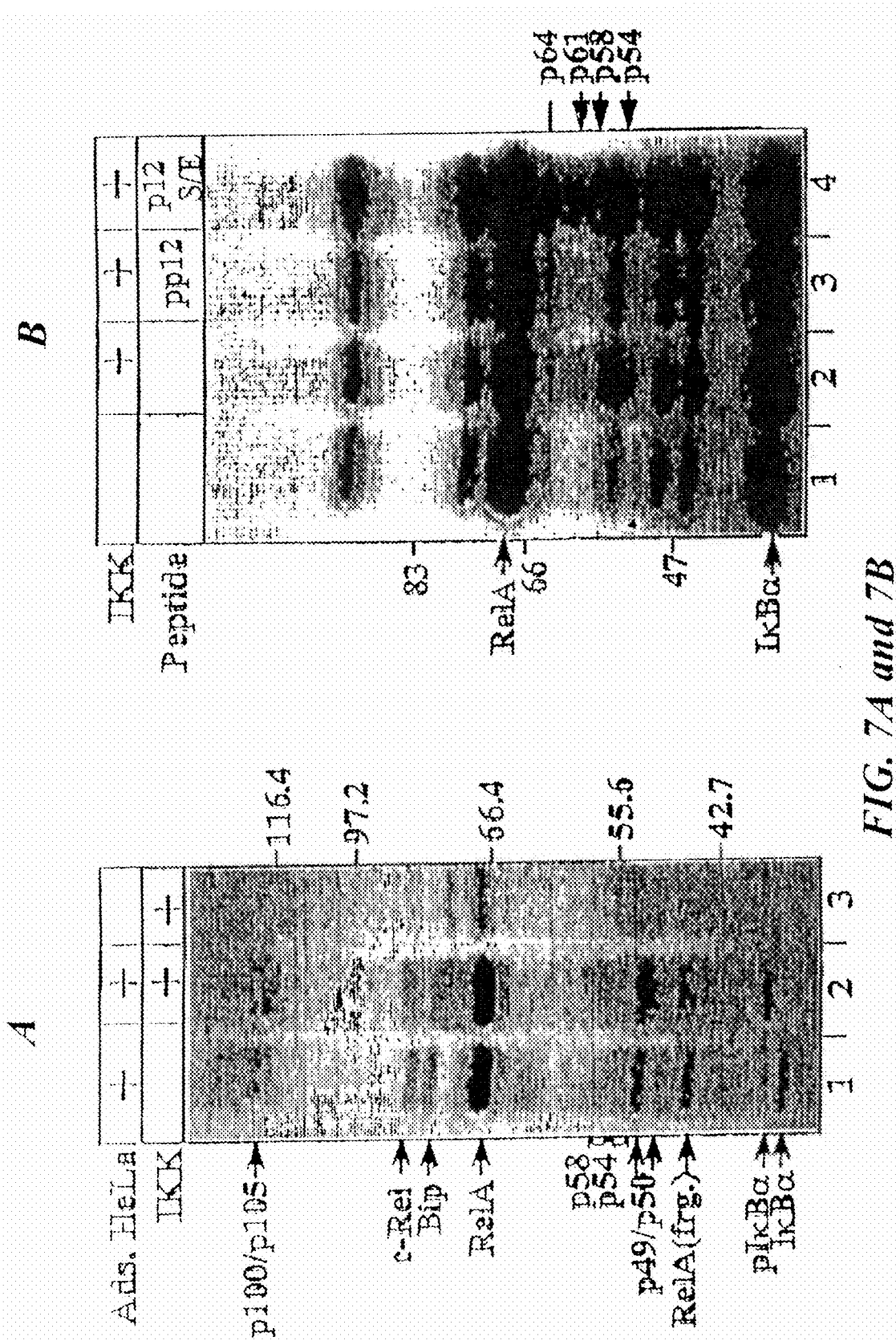
FIGS. 7A and 7B illustrate the identification of IκBα-binding proteins associated with ubiquitin-ligase activity.

To circumvent the possible masking of the putative pIκB-ubiquitin ligase, we replaced the ligase source with $^{35}$S-biosynthetically-labeled HeLa lysate and traced the IκBα-associated proteins by SDS-PAGE analysis and autoradiography (FIG. 7B). In parallel, the various fractions were tested for their ubiquitin-ligase capacity. The band-pattern of the active fraction (lane 2) was compared with that of the non-active one (lane 1). Four $^{35}$S-protein bands with a molecular mass of 54, 58, 61 and 64 kD were distinguished in lane 2. Some of these protein bands could represent components of the ubiquitin ligase that recognizes pIκBα directly whereas others might have associated with pIκBα indirectly or with another component of the IKK-phosphorylated complex. To sort out the ligase component that recognizes pIκBα directly, pp12 or the control peptide p12S/E was added to the radiolabeled HeLa lysate, which was then incubated with the immuno-bound IκBα/NF-κB complex. A comparison of the eluted fractions showed that of the four distinctive bands present only in fraction 2, three bands were eliminated by the specific pp12 peptide (p54, p58 and p61), whereas only the 64 kD band persisted in the presence of pp12 (FIG. 7B, compare lanes 2 and 3). The control peptide did not affect the association of any of the distinctive proteins with pIκBα (lane 4). Two of the pIκBα interacting proteins, p58 and p54. were consistently present and always associated with the specific ubiquitin-ligase activity.

Example 5

Identification of Human E3 Ubiquitin Ligase

This Example illustrates the isolation and characterization of human E3 ubiquitin ligase.

The 54 and 58 kD bands described in the previous Example were excised from a ligase-positive and a ligase-negative (HeLa lysate incubated with a non-phosphorylated IκBα-complex) lane, the proteins digested in situ (Shevchenko et al., *Anal. Chem.* 68:850-858, 1996) and the tryptic peptides thus obtained were sequenced by nanoelectrospray mass spectrometry (Wilm et al., *Nature* 379:466-469, 1996). Protein bands were reduced in-gel, S-alkylated and digested in-gel with an excess of trypsin (overnight at room temperature) as described (Shevchenko et al., *Anal. Chem.* 68:850-858, 1996; Wilm et al., *Nature* 379:466-469, 1996). Pieces of gel were extracted and the resulting peptide mixtures were concentrated and desalted, using a micro-column containing 50 nl of Poros R2 material (Perceptive Biosystems, Framingham, Mass.). Peptides were eluted with 1 μl of 60% methanol, 5% formic acid directly into a nanoelectrospray needle. Nanoelectrospray spectra were recorded on a quadrupole time-of-flight mass spectrometer (QqTOF, Perkin-Elmer Sciex, Toronto, Canada). Peptide sequence tags (Mann and Wilm, *Anal. Chem.* 66:4390-4399, 1994) were assembled from fragmentation spectra and searched against a non redundant protein sequence database (nrdb) maintained at the European BioInformatics Institute (EBI, Hinxton Park, England) using the program PeptideSearch (Mann and Wilm, *Anal. Chem.* 66:4390-4399, 1994).

Figures 8A, 8B, 8C, 8D:
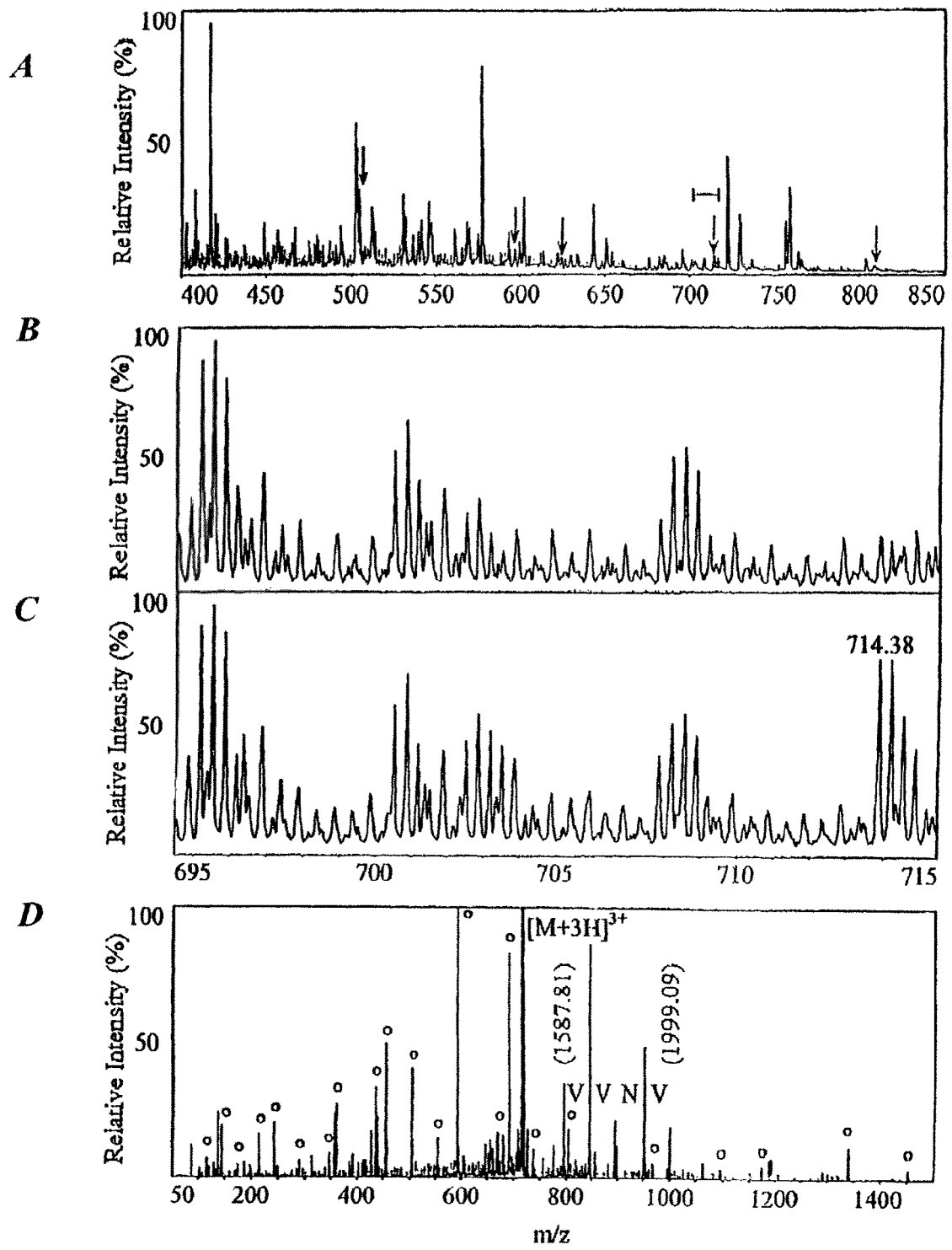
FIGS. 8A-8D show the results of a mass-spectrum analysis of ubiquitin-ligase associated p54.

Mass spectra of the 54 kD gel band revealed a complex peptide mixture (FIG. 8A) from which several peptides were selected for fragmentation. Proteins identified by peptide sequence tag searching (Mann and Wilm, *Anal. Chem.* 66:4390-4399, 1994) included NF-κB1 (p50). IκB kinase α, IκBε, RelB, tubulin beta-1 chain, and thyroid receptor initiator binding protein. To identify the protein associated with the E3 activity, additional peptides, present in small amounts, were selected for sequencing by comparing the spectrum of the 54 kD bands from the active fraction with that of a similar band from the non-active one (FIG. 8B). The peptide sequence tag (1587.81) VVNV (SEQ ID NO:23) (1999.09) was derived from the fragmentation spectrum shown in FIG. 8C and unambiguously identified as AAVNVVDFDDKYIV-SAS (SEQ ID NO:24). Further spectra identified the peptides LEGHEELVR (SEQ ID NO:25), LVVSGSSDNTIR (SEQ ID NO:26), IQDIETIESNWR (SEQ ID NO:27) and VISEGM-LWK (SEQ ID NO:28). The first four fragments have sequences present within the human F-box/WD protein β-TrCP (Margottin et al., *Mol. Cell* 1:565-574, 1998). However, the fifth peptide (VISEGMLWK (SEQ ID NO:28)) matches that of a peptide from the Drosophila Slimb protein (see Jiang and Struhl, *Nature* 391:493-496, 1998), which is highly homologous to human β-TrCP. Further sequencing identified the human E3 ubiquitin ligase nucleotide sequence provided in FIG. 9 (SEQ ID NO: 15), and the predicted protein sequence provided in FIG. 10 (SEQ ID NO: 16). Thus, the human E3 ubiquitin ligase appears to be a novel member of the β-TrCP/Slimb family of homologous proteins.

Example 6

Further Characterization of E3 Ubiquitin Ligase Activity

This Example further illustrates the ubiquitin ligase activity of the human E3 ubiquitin ligase family members β-TrCP and Slimb.

The ability of these proteins to bind pIκBα specifically and assist in its ubiquitination was examined in a cell-free system. The IκBα/NF-κB complex was immunopurified from HeLa cells and the immune complex was either phosphorylated with IKK2-EE or mock-phosphorylated as described above. It was then incubated with the following immobilized FLAG-tagged E3 family members immunoprecipitated from transfected 293 cells: mouse β-TrCP (mβ-TrCP), human β-TrCP (hβ-TrCP), human β-TrCP with a deletion of the F box region residues 122-168 (Δβ-TrCP) and the Drosophila Slimb protein. The bound material was analyzed by Western blotting with anti-IκBα and anti-FLAG antibodies. All of these proteins exclusively bound IKK-phosphorylated, but not mock-phosphorylated, IκBα (see FIG. 11A). However, the human and mouse β-TrCP bound IκBα far better than the highly homologous Drosophila protein (compare lanes 2, 4, 6 and 8). Δβ-TrCP bound pIκBα even better than the wild type protein, indicating that the F-box region was dispensable for binding. Furthermore, β-TrCP binding was abrogated by a peptide representing the pIκBα recognition motif (pp10; DRHDS(PO$_3$)GLDS(PO$_3$)M (SEQ ID NO:29); see FIG. 11B, lane 3), but not by the control peptide (lane 4), specifying the site of pIκBα recognition of the conserved DS(PO$_3$)GLDS(PO$_3$) (SEQ ID NO:30) sequence.

Figure 11A:
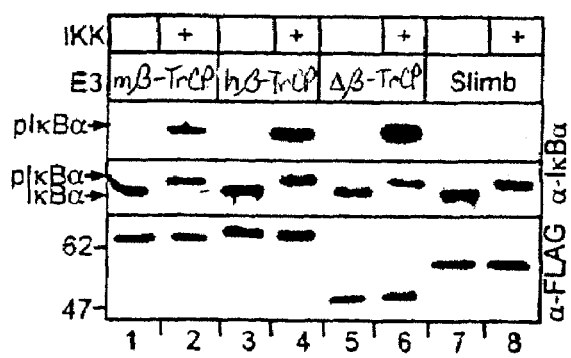
FIGS. 11A-11C are Western blots illustrating binding and ubiquitination specificity of E3 ubiquitin ligase family members. Within these figures, mβ-TrCP indicates mouse β-TrCP, hβ-TrCP indicates human β-TrCP, Δβ-TrCP indicates human β-TrCP with a deletion of the F box region and Slimb indicates the Drosophila Slimb protein.

To evaluate the effect of binding on ubiquitination, the E3 family members and the deletion mutant were used as a source of E3 activity in pIκBα ubiquitination. In the presence of E1 and E2 (UBC5C), the wild type β-TrCP proteins facilitated the ubiquitination of pIκBα, but not of the non-phosphorylated IκBα (see FIG. 11C, lanes 1-4). Δβ-TrCP, devoid of the F-box protein-protein interaction module, failed to promote ubiquitination (lanes 7 and 8), in spite of its binding capacity (FIG. 11A, lane 6). Although Slimb facilitated some pIκBα ubiquitination, it was at least ten-fold less efficient than the human and mouse β-TrCP (based on similar FLAG-tag expression levels), corresponding to its weaker activity.

Figure 11B:
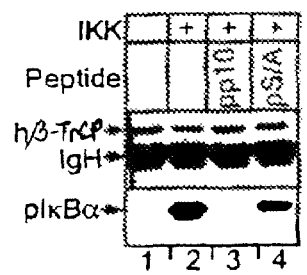
Figure 11C:
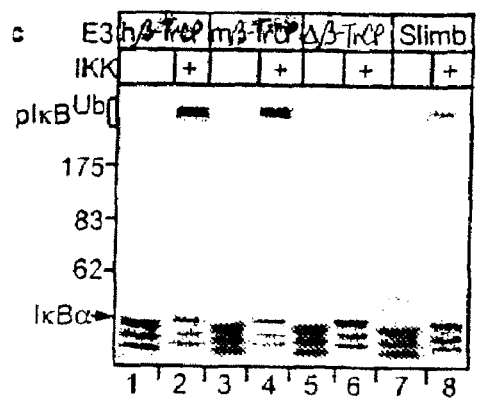
Figure 12A:
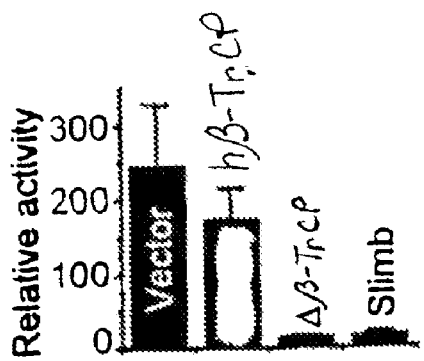
FIGS. 12A and 12B illustrate inhibition of IκBα degradation and NF-κB activation by overexpression of Δβ-TrCP, a dominant negative molecule.
Figure 12B:
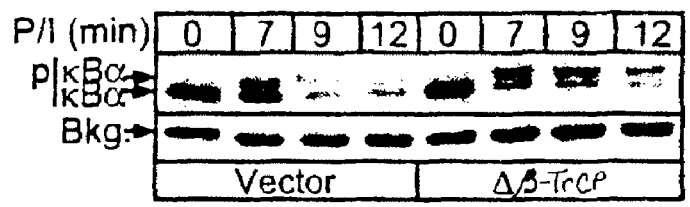

The modular design of these family members and the in vitro analysis described herein suggested that deletion of the F-box would result in a protein that functions as a dominant negative molecule in vivo. In fact, transient over-expression of the Δβ-TrCP inhibited the degradation of endogenous IκBα in stimulated Jurkat cells, resulting in accumulation of pIκBα (FIG. 12A). Consequently, activation of NF-κB was inhibited (FIG. 12B). NF-κB activation was specific, as Δβ-TrCP did not affect activation of an NF-AT reporter. Of note is the fact that NF-κB inhibition was also observed with wild type Slimb, whereas the expression of wild type human β-TrCP was not inhibitory (FIG. 12B). Therefore, overexpression of wild type Slimb has a dominant negative effect on NF-κB activation, probably linked to its relatively poor pIκBα ubiquitination activity (FIG. 11B).

From the foregoing it will be appreciated that, although specific embodiments of the invention have been described herein for purposes of illustration, various modifications may be made without deviating from the spirit and scope of the invention. Accordingly, the invention is not limited except as by the appended claims.

SUMMARY OF SEQUENCE LISTING

SEQ ID NO:1 is amino acid sequence of IκBα
SEQ ID NO:2 is DNA sequence of IκBα
SEQ ID NO:3 is amino acid sequence of IκBβ
SEQ ID NO:4 is DNA sequence of IκBβ
SEQ ID NO:5 is amino acid sequence of pp7
SEQ ID NO:6 is amino acid sequence of pp11
SEQ ID NO:7 is amino acid sequence of pp15
SEQ ID NO:8 is amino acid sequence of pp19
SEQ ID NO:9 is amino acid sequence of pp21
SEQ ID NO:10 is amino acid sequence of phospho-Fos peptide
SEQ ID NO:11 is amino acid sequence of pp21 S/A
SEQ ID NO:12 is amino acid sequence of HA-tagged IκBα
SEQ ID NO:13 is amino acid sequence of HA-tagged S32, 36 IκBα
SEQ ID NO:14 is amino acid sequence of HA-tagged IκBβ
SEQ ID NO:15 is DNA sequence of human E3 ubiquitin ligase
SEQ ID NO:16 is predicted amino acid sequence of human E3 ubiquitin ligase
SEQ ID NO:17 is DNA sequence of human β-TrCP
SEQ ID NO:18 is amino acid sequence of human E3 β-TrCP
SEQ ID NO:19 is phosphorylation site of IκBα
SEQ ID NO:20 is retrieved β-TrCP sequence
SEQ ID NO:21 is amino acid sequence of cognate p64 peptide
SEQ ID NO:22 is amino acid sequence of pIκBα peptide pp12
SEQ ID NO:23 is peptide sequence tag of human E3 ubiquitin ligase
SEQ ID NO:24 is peptide from human E3 ubiquitin ligase
SEQ ID NO:25 is peptide from human E3 ubiquitin ligase
SEQ ID NO:26 is peptide from human E3 ubiquitin ligase
SEQ ID NO:27 is peptide from human E3 ubiquitin ligase
SEQ ID NO:28 is peptide from human E3 ubiquitin ligase
SEQ ID NO:29 is amino acid sequence of pIκBα recognition motif
SEQ ID NO:30 is conserved pIκBα sequence

The invention claimed is:

1. A method for screening for an agent that modulates NF-κB activity, comprising the steps of:
   (a) contacting a candidate agent with a polypeptide comprising SEQ ID NO: 18, wherein the polypeptide enhances ubiquitination of phosphorylated IκB, under conditions and for a time sufficient to permit interaction between the polypeptide and candidate agent; and
   (b) subsequently evaluating the ability of the polypeptide to enhance ubiquitination of phosphorylated IκB, relative to the ability of the polypeptide to enhance ubiquitination of phosphorylated IκB in the absence of said candidate agent using a negative control, wherein said negative control is a mutant polypeptide consisting of SEQ ID NO:18, wherein F box residues 122-168 are deleted;

and therefrom identifying an agent that modulates NF-κB activity.

2. The method according to claim 1, wherein the candidate agent is a small molecule present within a combinatorial library.

3. The method of claim 1, wherein the candidate agent is a peptide.

4. The method of claim 1, wherein said conditions additionally comprise a peptidase inhibitor.

5. The method of claim 1, wherein the candidate agent is an antibody.

* * * * *

SEQUENCE LISTING

```
<160> NUMBER OF SEQ ID NOS: 30

<210> SEQ ID NO 1
<211> LENGTH: 317
<212> TYPE: PRT
<213> ORGANISM: Homo sapiens

<400> SEQUENCE: 1

Met Phe Gln Ala Ala Glu Arg Pro Gln Glu Trp Ala Met Glu Gly Pro
  1               5                  10                  15

Arg Asp Gly Leu Lys Lys Glu Arg Leu Leu Asp Asp Arg His Asp Ser
                 20                  25                  30

Gly Leu Asp Ser Met Lys Asp Glu Glu Tyr Glu Gln Met Val Lys Glu
             35                  40                  45

Leu Gln Glu Ile Arg Leu Glu Pro Gln Glu Val Pro Arg Gly Ser Glu
         50                  55                  60

Pro Trp Lys Gln Gln Leu Thr Glu Asp Gly Asp Ser Phe Leu His Leu
 65                  70                  75                  80

Ala Ile Ile His Glu Glu Lys Ala Leu Thr Met Glu Val Ile Arg Gln
                 85                  90                  95

Val Lys Gly Asp Leu Ala Phe Leu Asn Phe Gln Asn Asn Leu Gln Gln
                100                 105                 110

Thr Pro Leu His Leu Ala Val Ile Thr Asn Gln Pro Glu Ile Ala Glu
            115                 120                 125
```

```
Ala Leu Leu Gly Ala Gly Cys Asp Pro Glu Leu Arg Asp Phe Arg Gly
130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Leu Gly Gln Leu
                260                 265                 270

Thr Leu Glu Asn Leu Gln Met Leu Pro Glu Ser Glu Asp Glu Glu Ser
            275                 280                 285

Tyr Asp Thr Glu Ser Glu Phe Thr Glu Phe Thr Glu Asp Glu Leu Pro
        290                 295                 300

Tyr Asp Asp Cys Val Phe Gly Gly Gln Arg Leu Thr Leu
305                 310                 315

<210> SEQ ID NO 2
<211> LENGTH: 1550
<212> TYPE: DNA
<213> ORGANISM: Homo sapiens

<400> SEQUENCE: 2
tgccgccgtc ccgcccgcca gcgccccagc gaggaagcag cgcgcagccc gcggcccagc      60
gcacccgcag cagcgcccgc agctcgtccg cgccatgttc caggcggccg agcgccccca     120
ggagtgggcc atggagggcc cccgcgacgg gctgaagaag gagcggctac tggacgaccg     180
ccacgacagc ggcctggact ccatgaaaga cgaggagtac gagcagatgg tcaaggagct     240
gcaggagatc cgcctcgagc cgcaggaggt gccgcgcggc tcggagccct ggaagcagca     300
gctcaccgag acggggact cgttcctgca cttggccatc atccatgaag aaaaggcact     360
gaccatggaa gtgatccgcc aggtgaaggg agacctggct ttcctcaact tccagaacaa     420
cctgcagcag actccactcc acttggctgt gatcaccaac cagccagaaa ttgctgaggc     480
acttctggga gctggctgtg atcctgagct ccgagacttt cgaggaaata cccccctaca     540
ccttgcctgt gagcagggct gcctggccag cgtgggagtc ctgactcagt cctgcaccac     600
cccgcacctc cactccatcc tgaaggctac caactacaat ggccacacgt gtctacactt     660
agcctctatc catggctacc tgggcatcgt ggagcttttg gtgtccttgg gtgctgatgt     720
caatgctcag gagccctgta atggccggac tgcccttcac ctcgcagtgg acctgcaaaa     780
tcctgacctg gtgtcactcc tgttgaagtg tggggctgat gtcaacagag ttacctacca     840
gggctattct ccctaccagc tcacctgggg ccgcccaagc acccggatac agcagcagct     900
gggccagctg acactagaaa accttcagat gctgccagag agtgaggatg aggagagcta     960
tgacacagag tcagagttca cggagttcac agaggacgag ctgccctatg atgactgtgt    1020
gtttggaggc cagcgtctga cgttatgagt gcaaggggc tgaaagaaca tggacttgta    1080
```

```
tatttgtaca aaaaaaagt tttattttc taaaaaaga aaaagaaga aaaaatttaa   1140 agggtgtact tatatccaca ctgcacactg cctagcccaa aacgtcttat tgtggtagga   1200
tcagccctca ttttgttgct tttgtgaact ttttgtaggg gacgagaaag atcattgaaa   1260
ttctgagaaa acttctttta aacctcacct ttgtggggtt tttggagaag gttatcaaaa   1320
atttcatgga aggaccacat tttatattta ttgtgcttcg agtgactgac cccagtggta   1380
tcctgtgaca tgtaacagcc aggagtgtta agcgttcagt gatgtggggt gaaaagttac   1440
tacctgtcaa ggtttgtgtt accctcctgt aaatggtgta cataatgtat tgttggtaat   1500 tatttggta cttttatgat gtatatttat taaagagatt tttacaaatg   1550
```

<210> SEQ ID NO 3
<211> LENGTH: 359
<212> TYPE: PRT
<213> ORGANISM: Homo sapiens

<400> SEQUENCE: 3

```
Met Ala Gly Val Ala Cys Leu Gly Lys Thr Ala Asp Ala Asp Glu Trp
 1               5                  10                  15

Cys Asp Ser Gly Leu Gly Ser Leu Gly Pro Asp Ala Ala Ala Pro Gly
            20                  25                  30

Gly Pro Gly Leu Gly Ala Glu Leu Gly Pro Glu Leu Ser Trp Ala Pro
        35                  40                  45

Leu Val Phe Gly Tyr Val Thr Glu Asp Gly Asp Thr Ala Leu His Leu
    50                  55                  60

Ala Val Ile His Gln His Glu Pro Phe Leu Asp Phe Leu Leu Gly Phe
65                  70                  75                  80

Ser Ala Gly His Glu Tyr Leu Asp Leu Gln Asn Asp Leu Gly Gln Thr
                85                  90                  95

Ala Leu His Leu Ala Ala Ile Leu Gly Glu Ala Ser Thr Val Glu Lys
            100                 105                 110

Leu Tyr Ala Ala Gly Ala Gly Val Leu Val Ala Glu Arg Gly Gly His
        115                 120                 125

Thr Ala Leu His Leu Ala Cys Arg Val Arg Ala His Thr Cys Ala Cys
    130                 135                 140

Val Leu Leu Gln Pro Arg Pro Ser His Pro Arg Asp Ala Ser Asp Thr
145                 150                 155                 160

Tyr Leu Thr Gln Ser Gln Asp Cys Thr Pro Asp Thr Ser His Ala Pro
                165                 170                 175

Ala Ala Val Asp Ser Gln Pro Asn Pro Glu Asn Glu Glu Pro Arg
            180                 185                 190

Asp Glu Asp Trp Arg Leu Gln Leu Glu Ala Glu Asn Tyr Asp Gly His
        195                 200                 205

Thr Pro Leu His Val Ala Val Ile His Lys Asp Ala Glu Met Val Arg
    210                 215                 220

Leu Leu Arg Asp Ala Gly Ala Asp Leu Asn Lys Pro Glu Pro Thr Cys
225                 230                 235                 240

Gly Arg Thr Pro Leu His Leu Ala Val Glu Ala Gln Ala Ala Ser Val
                245                 250                 255

Leu Glu Leu Leu Leu Lys Ala Gly Ala Asp Pro Thr Ala Arg Met Tyr
            260                 265                 270

Gly Gly Arg Thr Pro Leu Gly Ser Ala Leu Leu Arg Pro Asn Pro Ile
        275                 280                 285

Leu Ala Arg Leu Leu Arg Ala His Gly Ala Pro Glu Pro Glu Asp Glu
    290                 295                 300
```

```
Asp Asp Lys Leu Ser Pro Cys Ser Ser Gly Ser Asp Ser Asp Ser
305                 310                 315                 320

Asp Asn Arg Asp Glu Gly Asp Glu Tyr Asp Asp Ile Val Val His Ser
                325                 330                 335

Gly Arg Ser Gln Asn Arg Gln Pro Pro Ser Pro Ala Ser Lys Pro Leu
            340                 345                 350

Pro Asp Asp Pro Asn Pro Ala
        355

<210> SEQ ID NO 4
<211> LENGTH: 1212
<212> TYPE: DNA
<213> ORGANISM: Homo sapiens

<400> SEQUENCE: 4
gcgcactgga gctcatcgca gagcccagcg acaggcaggc gaccacaggg ggccacccga      60
ggtggctggg gccatggccg gggtcgcgtg cttggggaaa actgcggatg ccgatgaatg     120
gtgcgacagc ggcctgggct ctctaggtcc cgacgcagcg gctcccggag gaccaggtct     180
gggcgcagag cttggcccag agctgtcgtg ggcgccctta gtctttggct acgtcactga     240
ggatggggac acagccctgc acttggctgt gattcatcag catgagccct cctggatttt     300
cctcctgggc ttttccgccg ccacgagta ccttgacctg cagaatgacc taggccaaac      360
agccctgcat ctagcagcca tccttgggga ggcatctaca gtagagaagt tgtatgcagc     420
cggtgcagga gtgttggtgg ctgagagagg gggccacacg gcattgcact ggcctgccg      480
ggtcagggca cacacgtgcg cgtgcgtact gctccagccc cgtcccagcc acccaagaga     540
tgcctcagat acctacctca ctcagagcca ggactgtacc ccagacacca gccatgcccc     600
tgctgccgtg gattcccaac ccaacccaga gaacgaagag gagccgcgtg atgaagactg     660
gaggctacaa ctagaagctg aaaactatga tggccatacc ccactccatg tagctgtcat     720
ccacaaagat gcagagatgg tccggctgct cagggatgcc ggagccgacc tcaataaacc     780
ggagcctacg tgtggccgga cccctctgca cctggcagta aagcccagg cagccagcgt      840
gctggaactt ctcctgaaag ccggtgctga ccccaccgcc cgcatgtatg ggggccgcac     900
cccgcttggc agtgccctgc tccggcccaa ccccatcctt gcccgcctcc tccgtgcaca     960
tgggccccct gaacctgagg acgaggacga taagcttagc ccttgcagca gcagcggcag    1020
cgacagtgac agtgacaaca gagatgaggg cgatgaatat gatgacatcg tggttcacag    1080
tggcaggagc caaaaccgac aaccgccttc cccggcatcc aaacctcttc ctgatgaccc    1140
caaccctgcc tgacttaagt gctaatatta atataatttc caacttaata aaattgcaga    1200
cctgacaacc ag                                                        1212

<210> SEQ ID NO 5
<211> LENGTH: 8
<212> TYPE: PRT
<213> ORGANISM: Homo sapiens

<400> SEQUENCE: 5

Cys Asp Ser Gly Leu Asp Ser Met
1               5

<210> SEQ ID NO 6
<211> LENGTH: 12
<212> TYPE: PRT
<213> ORGANISM: Homo sapiens
```

```
<400> SEQUENCE: 6

Cys Asp Asp Arg His Asp Ser Gly Leu Asp Ser Met
1               5                   10

<210> SEQ ID NO 7
<211> LENGTH: 16
<212> TYPE: PRT
<213> ORGANISM: Homo sapiens

<400> SEQUENCE: 7

Cys Asp Asp Arg His Asp Ser Gly Leu Asp Ser Met Lys Asp Glu Glu
1               5                   10                  15

<210> SEQ ID NO 8
<211> LENGTH: 20
<212> TYPE: PRT
<213> ORGANISM: Homo sapiens

<400> SEQUENCE: 8

Cys Glu Arg Leu Leu Asp Asp Arg His Asp Ser Gly Leu Asp Ser Met
1               5                   10                  15

Lys Asp Glu Glu
            20

<210> SEQ ID NO 9
<211> LENGTH: 22
<212> TYPE: PRT
<213> ORGANISM: Homo sapiens

<400> SEQUENCE: 9

Cys Lys Lys Glu Arg Leu Leu Asp Asp Arg His Asp Ser Gly Leu Asp
1               5                   10                  15

Ser Met Lys Asp Glu Glu
            20

<210> SEQ ID NO 10
<211> LENGTH: 19
<212> TYPE: PRT
<213> ORGANISM: Homo sapiens

<400> SEQUENCE: 10

Ile Gly Arg Arg Gly Lys Val Glu Gln Leu Ser Pro Glu Glu Glu
1               5                   10                  15

Lys Arg Arg

<210> SEQ ID NO 11
<211> LENGTH: 22
<212> TYPE: PRT
<213> ORGANISM: Homo sapiens

<400> SEQUENCE: 11

Cys Lys Lys Glu Arg Leu Leu Asp Asp Arg His Asp Ala Gly Leu Asp
1               5                   10                  15

Ala Met Lys Asp Glu Glu
            20

<210> SEQ ID NO 12
<211> LENGTH: 347
<212> TYPE: PRT
<213> ORGANISM: Homo sapiens
```

<400> SEQUENCE: 12

```
Met Tyr Pro Tyr Asp Val Pro Asp Tyr Ala Met Tyr Pro Tyr Asp Val
  1               5                  10                  15

Pro Asp Tyr Ala Met Tyr Pro Tyr Asp Val Pro Asp Tyr Ala Met Phe
             20                  25                  30

Gln Ala Ala Glu Arg Pro Gln Glu Trp Ala Met Glu Gly Pro Arg Asp
         35                  40                  45

Gly Leu Lys Lys Glu Arg Leu Leu Asp Asp Arg His Asp Ser Gly Leu
     50                  55                  60

Asp Ser Met Lys Asp Glu Glu Tyr Glu Gln Met Val Lys Glu Leu Gln
 65                  70                  75                  80

Glu Ile Arg Leu Glu Pro Gln Glu Val Pro Arg Gly Ser Glu Pro Trp
                 85                  90                  95

Lys Gln Gln Leu Thr Glu Asp Gly Asp Ser Phe Leu His Leu Ala Ile
            100                 105                 110

Ile His Glu Glu Lys Ala Leu Thr Met Glu Val Ile Arg Gln Val Lys
        115                 120                 125

Gly Asp Leu Ala Phe Leu Asn Phe Gln Asn Asn Leu Gln Gln Thr Pro
    130                 135                 140

Leu His Leu Ala Val Ile Thr Asn Gln Pro Glu Ile Ala Glu Ala Leu
145                 150                 155                 160

Leu Gly Ala Gly Cys Asp Pro Glu Leu Arg Asp Phe Arg Gly Asn Thr
                165                 170                 175

Pro Leu His Leu Ala Cys Glu Gln Gly Cys Leu Ala Ser Val Gly Val
            180                 185                 190

Leu Thr Gln Ser Cys Thr Thr Pro His Leu His Ser Ile Leu Lys Ala
        195                 200                 205

Thr Asn Tyr Asn Gly His Thr Cys Leu His Leu Ala Ser Ile His Gly
    210                 215                 220

Tyr Leu Gly Ile Val Glu Leu Leu Val Ser Leu Gly Ala Asp Val Asn
225                 230                 235                 240

Ala Gln Glu Pro Cys Asn Gly Arg Thr Ala Leu His Leu Ala Val Asp
                245                 250                 255

Leu Gln Asn Pro Asp Leu Val Ser Leu Leu Lys Cys Gly Ala Asp
            260                 265                 270

Val Asn Arg Val Thr Tyr Gln Gly Tyr Ser Pro Tyr Gln Leu Thr Trp
        275                 280                 285

Gly Arg Pro Ser Thr Arg Ile Gln Gln Gln Leu Gly Gln Leu Thr Leu
    290                 295                 300

Glu Asn Leu Gln Met Leu Pro Glu Ser Glu Asp Glu Glu Ser Tyr Asp
305                 310                 315                 320

Thr Glu Ser Glu Phe Thr Glu Phe Thr Glu Asp Glu Leu Pro Tyr Asp
                325                 330                 335

Asp Cys Val Phe Gly Gly Gln Arg Leu Thr Leu
            340                 345
```

<210> SEQ ID NO 13
<211> LENGTH: 347
<212> TYPE: PRT
<213> ORGANISM: Homo sapiens

<400> SEQUENCE: 13

```
Met Tyr Pro Tyr Asp Val Pro Asp Tyr Ala Met Tyr Pro Tyr Asp Val
 1               5                  10                  15

Pro Asp Tyr Ala Met Tyr Pro Tyr Asp Val Pro Asp Tyr Ala Met Phe
                20                  25                  30

Gln Ala Ala Glu Arg Pro Gln Glu Trp Ala Met Glu Gly Pro Arg Asp
            35                  40                  45

Gly Leu Lys Lys Glu Arg Leu Leu Asp Asp Arg His Asp Ala Gly Leu
        50                  55                  60

Asp Ala Met Lys Asp Glu Glu Tyr Glu Gln Met Val Lys Glu Leu Gln
 65                  70                  75                  80

Glu Ile Arg Leu Glu Pro Gln Glu Val Pro Arg Gly Ser Glu Pro Trp
                85                  90                  95

Lys Gln Gln Leu Thr Glu Asp Gly Asp Ser Phe Leu His Leu Ala Ile
            100                 105                 110

Ile His Glu Glu Lys Ala Leu Thr Met Glu Val Ile Arg Gln Val Lys
        115                 120                 125

Gly Asp Leu Ala Phe Leu Asn Phe Gln Asn Asn Leu Gln Gln Thr Pro
130                 135                 140

Leu His Leu Ala Val Ile Thr Asn Gln Pro Glu Ile Ala Glu Ala Leu
145                 150                 155                 160

Leu Gly Ala Gly Cys Asp Pro Glu Leu Arg Asp Phe Arg Gly Asn Thr
                165                 170                 175

Pro Leu His Leu Ala Cys Glu Gln Gly Cys Leu Ala Ser Val Gly Val
            180                 185                 190

Leu Thr Gln Ser Cys Thr Thr Pro His Leu His Ser Ile Leu Lys Ala
        195                 200                 205

Thr Asn Tyr Asn Gly His Thr Cys Leu His Leu Ala Ser Ile His Gly
210                 215                 220

Tyr Leu Gly Ile Val Glu Leu Leu Val Ser Leu Gly Ala Asp Val Asn
225                 230                 235                 240

Ala Gln Glu Pro Cys Asn Gly Arg Thr Ala Leu His Leu Ala Val Asp
                245                 250                 255

Leu Gln Asn Pro Asp Leu Val Ser Leu Leu Lys Cys Gly Ala Asp
            260                 265                 270

Val Asn Arg Val Thr Tyr Gln Gly Tyr Ser Pro Tyr Gln Leu Thr Trp
        275                 280                 285

Gly Arg Pro Ser Thr Arg Ile Gln Gln Gln Leu Gly Gln Leu Thr Leu
290                 295                 300

Glu Asn Leu Gln Met Leu Pro Glu Ser Glu Asp Glu Ser Tyr Asp
305                 310                 315                 320

Thr Glu Ser Glu Phe Thr Glu Phe Thr Glu Asp Glu Leu Pro Tyr Asp
                325                 330                 335

Asp Cys Val Phe Gly Gly Gln Arg Leu Thr Leu
            340                 345
```

<210> SEQ ID NO 14
<211> LENGTH: 389
<212> TYPE: PRT
<213> ORGANISM: Homo sapiens

```
<400> SEQUENCE: 14

Met Tyr Pro Tyr Asp Val Pro Asp Tyr Ala Met Tyr Pro Tyr Asp Val
  1               5                  10                  15

Pro Asp Tyr Ala Met Tyr Pro Tyr Asp Val Pro Asp Tyr Ala Met Ala
             20                  25                  30

Gly Val Ala Cys Leu Gly Lys Thr Ala Asp Ala Asp Glu Trp Cys Asp
         35                  40                  45

Ser Gly Leu Gly Ser Leu Gly Pro Asp Ala Ala Pro Gly Gly Pro
     50                  55                  60

Gly Leu Gly Ala Glu Leu Gly Pro Glu Leu Ser Trp Ala Pro Leu Val
 65                  70                  75                  80

Phe Gly Tyr Val Thr Glu Asp Gly Asp Thr Ala Leu His Leu Ala Val
                 85                  90                  95

Ile His Gln His Glu Pro Phe Leu Asp Phe Leu Leu Gly Phe Ser Ala
                100                 105                 110

Gly His Glu Tyr Leu Asp Leu Gln Asn Asp Leu Gly Gln Thr Ala Leu
            115                 120                 125

His Leu Ala Ala Ile Leu Gly Glu Ala Ser Thr Val Glu Lys Leu Tyr
130                 135                 140

Ala Ala Gly Ala Gly Val Leu Val Ala Glu Arg Gly Gly His Thr Ala
145                 150                 155                 160

Leu His Leu Ala Cys Arg Val Arg Ala His Thr Cys Ala Cys Val Leu
                165                 170                 175

Leu Gln Pro Arg Pro Ser His Pro Arg Asp Ala Ser Asp Thr Tyr Leu
            180                 185                 190

Thr Gln Ser Gln Asp Cys Thr Pro Asp Thr Ser His Ala Pro Ala Ala
            195                 200                 205

Val Asp Ser Gln Pro Asn Pro Glu Asn Glu Glu Pro Arg Asp Glu
210                 215                 220

Asp Trp Arg Leu Gln Leu Glu Ala Glu Asn Tyr Asp Gly His Thr Pro
225                 230                 235                 240

Leu His Val Ala Val Ile His Lys Asp Ala Glu Met Val Arg Leu Leu
                245                 250                 255

Arg Asp Ala Gly Ala Asp Leu Asn Lys Pro Glu Pro Thr Cys Gly Arg
            260                 265                 270

Thr Pro Leu His Leu Ala Val Glu Ala Gln Ala Ala Ser Val Leu Glu
            275                 280                 285

Leu Leu Leu Lys Ala Gly Ala Asp Pro Thr Ala Arg Met Tyr Gly Gly
290                 295                 300

Arg Thr Pro Leu Gly Ser Ala Leu Leu Arg Pro Asn Pro Ile Leu Ala
305                 310                 315                 320

Arg Leu Leu Arg Ala His Gly Ala Pro Glu Pro Glu Asp Glu Asp Asp
                325                 330                 335

Lys Leu Ser Pro Cys Ser Ser Gly Ser Asp Ser Asp Ser Asp Asn
            340                 345                 350

Arg Asp Glu Gly Asp Glu Tyr Asp Asp Ile Val Val His Ser Gly Arg
            355                 360                 365

Ser Gln Asn Arg Gln Pro Pro Ser Pro Ala Ser Lys Pro Leu Pro Asp
370                 375                 380

Asp Pro Asn Pro Ala
385
```

<210> SEQ ID NO 15
<211> LENGTH: 4230
<212> TYPE: DNA
<213> ORGANISM: Homo sapiens

<400> SEQUENCE: 15

| | | | | | | |
|---|---|---|---|---|---|---|
| gcgaggcggg | gccgccgggg | ccgccatgga | gcccgactcg | gtgattgagg | acaagaccat | 60 |
| cgagctcatg | tgttctgtgc | caaggtcttt | gtggctaggc | tgcgccaacc | tggtagagag | 120 |
| catgtgcgca | ctgagttgcc | tgcagagcat | gcccagtgtc | agatgtctcc | agataagtaa | 180 |
| tggaacatca | tctgtgatcg | tctccagaaa | gaggccatca | aaggaaact | atcaaaaaga | 240 |
| aaaagacttg | tgtattaaat | attttgacca | gtggtctgaa | tcagatcaag | tggaatttgt | 300 |
| ggaacatctt | atttcacgaa | tgtgtcatta | tcagcatgga | catattaact | cttacctgaa | 360 |
| gcccatgttg | cagcgggact | ttattaccgc | tttaccagag | caaggcttag | atcacatagc | 420 |
| agaaaacatt | ctttcgtacc | tggatgccag | gtctctgtgt | gcagcagagc | tggtatgtaa | 480 |
| agaatggcag | cgagtgatct | cagaaggaat | gcttttggaag | aagctgattg | aacgaatggt | 540 |
| acgcactgat | ccctatggaa | aaggactttc | agaaagaaga | gggtgggatc | agtacctgtt | 600 |
| taaaaacaga | cccacagatg | gccctccaaa | ttcattttat | aggtcattat | acccaaagat | 660 |
| tatccaggat | atagagacta | tagaatctaa | ctggcggtgt | ggacgacaca | acttgcagag | 720 |
| gattcagtgc | cgctctgaaa | atagtaaagg | tgtctactgt | ttacagtacg | atgatgaaaa | 780 |
| aattatcagt | ggcctacgag | ataattctat | taagatatgg | gataaaacca | gcctggaatg | 840 |
| tttgaaagtg | ttaacaggac | acacaggctc | tgtcctctgt | ctgcagtatg | atgagcgtgt | 900 |
| cattgtaact | ggctcttcag | attctacggt | gagagtgtgg | gatgtgaaca | cgggtgaagt | 960 |
| tcttaacaca | ttgatccacc | acaatgaggc | tgtattgcac | ttacgcttca | gcaatggact | 1020 |
| gatggtgacc | tgttccaagg | accgctccat | tgctgtgtgg | gacatggctt | ctgcgaccga | 1080 |
| catcacttta | cgccgtgtcc | tggttggcca | ccgggctgcc | gtcaatgtag | tagactttga | 1140 |
| cgacaagtac | atcgtgtctg | cctctggtga | caggaccatc | aaagtctgga | gcacgagcac | 1200 |
| ctgtgaattt | gttcgtactc | tcaatgggca | caagcggggc | attgcctgtc | tccagtacag | 1260 |
| ggatcgcctg | gttgttagtg | gatcatcaga | taataccatt | aggctctggg | atattgaatg | 1320 |
| tggtgcctgt | ttaagagtcc | tagagggaca | tgaagaattg | gtccgatgca | tccggtttga | 1380 |
| taacaagagg | attgtcagtg | gggcctatga | tgggaaaatt | aaagtttggg | acttgcaagc | 1440 |
| tgctcttgac | cctcgagccc | cagcaagcac | attgtgtttg | cgcacattgg | tggaacattc | 1500 |
| tggacgtgtg | tttcggctcc | agtttgatga | gtttcagatc | atcagcagct | cccatgatga | 1560 |
| cactattttg | atttgggatt | tcttaaatgt | gcctccagt | gcccagaatg | agacccgttc | 1620 |
| tccctccaga | acatacactt | acatctctag | ataacagtct | gcactttcac | ccgtttcagg | 1680 |
| gttttctagt | cttgaactac | tggctacgtg | gctaccaaat | gcctaaggga | gttcgttcac | 1740 |
| agctgagtta | tgaagctgga | attggttcta | gacgctgggg | agatgcaaag | cagcctaact | 1800 |
| cttcaagtac | cgacatttct | cacctctgat | tccggctctc | ctttgagaag | gagaccttag | 1860 |
| cttccccggc | ttcaagtaga | acagaagccc | gtttccttcc | ctcatcagtg | aaaaaatcta | 1920 |
| atgtttcaaa | tgtaaattgt | tcatagaaaa | ggaacataga | atctgtttta | cagaagtaaa | 1980 |
| tcgaccgtca | agagaagact | tggcctctaa | tttatattgc | tttgcacttt | ggtttgatat | 2040 |
| taagaaacag | cattcttctt | cagtgaaatt | ttgggtgcca | acacctacc | cagaatgtcc | 2100 |
| agggctttca | ttttcaaaag | ttagcattct | ccttttgacc | gtccaagtca | ttatgaattc | 2160 |

```
tgacttgttg tattaggaac atgttggaca gtggaaaatt ttctctggat tgttttagta    2220 atattttttgg gattatactt cctttctgta ccaatttctt ttaatttaaa gaactataag   2280
tcagttatat tatctaccaa caggtaatat agctctttct tttattaact gttctctgtc    2340
ccccaaccat ctcctgatat ttggtagagt aacacccttta tacgtgtgct tgcctcctaa   2400
tttaaaatac tgtattcgca tgtagatata atgtacataa cagtttaacc tcaaagttgc    2460
tggagtcagg gccccctgtg cttgagacac taatacagag tgtgttcgca cttagccatg    2520
ggctgggctc aagaacctga tacctgggtt gatgtggatt acctagaacc cttcctgcag    2580
tattcataca gtgttttttat tttgttgttg tcattgcgtg tgtgtggttt gtgtgtgttt   2640
ttaatgagaa tcttgtttta aaatgtaatt tctaaggttt aacaccaaaa tgttttattt    2700
gttgtggagt atatattata caatagagag gtaccttaaa cattttttgt tcttattctt    2760
tttctcataa gtactcctga gtacaagtgg tcacctccca tagtattcat ttggcttcgc    2820
tgtcaaaaat cattattctg tgcagtcgtg gccctgggaa ggggaaataa gaaggccctg    2880
ttgacgggct gtcttggctc tggaattcat gcatcctggc cttgccaagg ttctggcagg    2940
gcctgctggt gtgttggagc ctgcagggca ggtcaggctg gttcagaggc ccatgctgag    3000
gggtgggtgc tctgaagtgg agtgaagcct caagcccatg aatgccaccc cagtcatctc    3060
tggtgtcagc tgctgctgtg gccccagcag gttctcaaag ctcccaagtc ctccctacga    3120
cacagcccaa atgtgtaaat ggcactgttg ccctgacagt gcatggaaag gacgttggca    3180
tccaattggc actccttctc ccttattcaa tattaggttt gatttgccct tcgccattgt    3240
ttccaaagat caaggaatgt caataacatt ttaaaggacc aataaacagc ctcctataaa    3300
gtaaacctct tcccgtggaa gcacactcta ctactaaagg gaaggcccct gggctctgat    3360
ttgtcctttg cattgagaac ggtgtgggga tcagtgtgtg tgtatgtgat tgttttattg    3420
agttggcttt gctttttttag ttttttcttt aaaaataaaa tccttccttc ccatgttact   3480
aaattaattt atgttttttga gaggttgagt ctcaaagtgt aaacaataaa cctccattca   3540
taaggtggat gttgtaagct tgatggtggt tgtgaaagtg atttagcttt gaccacttttt   3600 catcctacag cttcaatatc aaactggtta ggaaagccca gggggaaggg aggggggcagg   3660 ggaggaggca attctgaatg aatgaatgga ttttttgttg tttttgcatg tttaatatag    3720
aagttcccct cgttccttgg gagatgatgg cctttgaata tgcagacaac ctttgaattg    3780
tgcctactaa attatagcag gggactttgg cacccaagga gttctgactt tctgggatta    3840
taatagtaat tcccagccat actctggact ttattttgct aaccataact gagcaaatgt    3900
aaattactgc tatattaatg ttttaaagca ctgggatagt ctaattctaa cttgtaatta    3960
attatgtttg ccaattatct gtttgaaata aatttgtgtc tgaacagcta ttgaaactgt    4020
taaattgtac agatattatt catgacagct ttgtactgtg gaatgtgctt aataaaaaac    4080
aaaaaagttt gacttttgtc cagtaaattg ctaagtaatg tcaataaatc gagtatgggt    4140
attatgcagt gcacctaatc tggcttcatg caattgttac ttcagctact gattcaaagc    4200
caatactctt aataaagtgt tgcaatactc                                     4230
```

<210> SEQ ID NO 16
<211> LENGTH: 542
<212> TYPE: PRT
<213> ORGANISM: Homo sapiens

```
<400> SEQUENCE: 16

Met Glu Pro Asp Ser Val Ile Glu Asp Lys Thr Ile Glu Leu Met Cys
 1               5                  10                  15

Ser Val Pro Arg Ser Leu Trp Leu Gly Cys Ala Asn Leu Val Glu Ser
            20                  25                  30

Met Cys Ala Leu Ser Cys Leu Gln Ser Met Pro Ser Val Arg Cys Leu
        35                  40                  45

Gln Ile Ser Asn Gly Thr Ser Ser Val Ile Val Ser Arg Lys Arg Pro
    50                  55                  60

Ser Glu Gly Asn Tyr Gln Lys Glu Lys Asp Leu Cys Ile Lys Tyr Phe
65                  70                  75                  80

Asp Gln Trp Ser Glu Ser Asp Gln Val Glu Phe Val Glu His Leu Ile
                85                  90                  95

Ser Arg Met Cys His Tyr Gln His Gly His Ile Asn Ser Tyr Leu Lys
            100                 105                 110

Pro Met Leu Gln Arg Asp Phe Ile Thr Ala Leu Pro Glu Gln Gly Leu
        115                 120                 125

Asp His Ile Ala Glu Asn Ile Leu Ser Tyr Leu Asp Ala Arg Ser Leu
    130                 135                 140

Cys Ala Ala Glu Leu Val Cys Lys Glu Trp Gln Arg Val Ile Ser Glu
145                 150                 155                 160

Gly Met Leu Trp Lys Lys Leu Ile Glu Arg Met Val Arg Thr Asp Pro
                165                 170                 175

Leu Trp Lys Gly Leu Ser Glu Arg Arg Gly Trp Asp Gln Tyr Leu Phe
            180                 185                 190

Lys Asn Arg Pro Thr Asp Gly Pro Pro Asn Ser Phe Tyr Arg Ser Leu
        195                 200                 205

Tyr Pro Lys Ile Ile Gln Asp Ile Glu Thr Ile Glu Ser Asn Trp Arg
    210                 215                 220

Cys Gly Arg His Asn Leu Gln Arg Ile Gln Cys Arg Ser Glu Asn Ser
225                 230                 235                 240

Lys Gly Val Tyr Cys Leu Gln Tyr Asp Asp Glu Lys Ile Ile Ser Gly
                245                 250                 255

Leu Arg Asp Asn Ser Ile Lys Ile Trp Asp Lys Thr Ser Leu Glu Cys
            260                 265                 270

Leu Lys Val Leu Thr Gly His Thr Gly Ser Val Leu Cys Leu Gln Tyr
        275                 280                 285

Asp Glu Arg Val Ile Val Thr Gly Ser Ser Asp Ser Thr Val Arg Val
    290                 295                 300

Trp Asp Val Asn Thr Gly Glu Val Leu Asn Thr Leu Ile His His Asn
305                 310                 315                 320

Glu Ala Val Leu His Leu Arg Phe Ser Asn Gly Leu Met Val Thr Cys
                325                 330                 335

Ser Lys Asp Arg Ser Ile Ala Val Trp Asp Met Ala Ser Ala Thr Asp
            340                 345                 350

Ile Thr Leu Arg Arg Val Leu Val Gly His Arg Ala Ala Val Asn Val
        355                 360                 365

Val Asp Phe Asp Asp Lys Tyr Ile Val Ser Ala Ser Gly Asp Arg Thr
    370                 375                 380

Ile Lys Val Trp Ser Thr Ser Thr Cys Glu Phe Val Arg Thr Leu Asn
385                 390                 395                 400

Gly His Lys Arg Gly Ile Ala Cys Leu Gln Tyr Arg Asp Arg Leu Val
                405                 410                 415
```

Val Ser Gly Ser Ser Asp Asn Thr Ile Arg Leu Trp Asp Ile Glu Cys
            420                 425                 430

Gly Ala Cys Leu Arg Val Leu Glu Gly His Glu Leu Val Arg Cys
        435                 440                 445

Ile Arg Phe Asp Asn Lys Arg Ile Val Ser Gly Ala Tyr Asp Gly Lys
450                 455                 460

Ile Lys Val Trp Asp Leu Gln Ala Ala Leu Asp Pro Arg Ala Pro Ala
465                 470                 475                 480

Ser Thr Leu Cys Leu Arg Thr Leu Val Glu His Ser Gly Arg Val Phe
                485                 490                 495

Arg Leu Gln Phe Asp Glu Phe Gln Ile Ile Ser Ser Ser His Asp Asp
                500                 505                 510

Thr Ile Leu Ile Trp Asp Phe Leu Asn Val Pro Pro Ser Ala Gln Asn
            515                 520                 525

Glu Thr Arg Ser Pro Ser Arg Thr Tyr Thr Tyr Ile Ser Arg
            530                 535                 540

<210> SEQ ID NO 17
<211> LENGTH: 2151
<212> TYPE: DNA
<213> ORGANISM: Homo sapiens

<400> SEQUENCE: 17

| | | | | | |
|---|---|---|---|---|---|
| tgcgttggct | gcggcctggc | accaaagggg | cggccccggc | ggagagcgga | cccagtggcc | 60 |
| tcggcgatta | tggaccccgc | cgaggcggtg | ctgcaagaga | aggcactcaa | gtttatgaat | 120 |
| tcctcagaga | gagaagactg | taataatggc | gaaccccta | ggaagataat | accagagaag | 180 |
| aattcactta | gacagacata | caacagctgt | gccagactct | gcttaaacca | agaaacagta | 240 |
| tgtttagcaa | gcactgctat | gaagactgag | aattgtgtgg | ccaaaacaaa | acttgccaat | 300 |
| ggcacttcca | gtatgattgt | gcccaagcaa | cggaaactct | cagcaagcta | tgaaaaggaa | 360 |
| aaggaactgt | gtgtcaaata | cttttgagcag | tggtcagagt | cagatcaagt | ggaatttgtg | 420 |
| gaacatctta | tatcccaaat | gtgtcattac | caacatgggc | acataaactc | gtatcttaaa | 480 |
| cctatgttgc | agagagattt | cataactgct | ctgccagctc | ggggattgga | tcatatcgct | 540 |
| gagaacattc | tgtcatacct | ggatgccaaa | tcactatgtg | ctgctgaact | tgtgtgcaag | 600 |
| gaatggtacc | gagtgacctc | tgatggcatg | ctgtggaaga | agcttatcga | gaaatggtc | 660 |
| aggacagatt | ctctgtggag | aggcctggca | gaacgaagag | gatggggaca | gtatttattc | 720 |
| aaaaacaaac | ctcctgacgg | gaatgctcct | cccaactctt | tttatagagc | actttatcct | 780 |
| aaaattatac | aagacattga | gacaatagaa | tctaattgga | gatgtggaag | acatagttta | 840 |
| cagagaattc | actgccgaag | tgaaacaagc | aaaggagttt | actgtttaca | gtatgatgat | 900 |
| cagaaaatag | taagcggcct | tcgagacaac | acaatcaaga | tctgggataa | aaacacattg | 960 |
| gaatgcaagc | gaattctcac | aggccataca | ggttcagtcc | tctgtctcca | gtatgatgag | 1020 |
| agagtgatca | taacaggatc | atcggattcc | acggtcagag | tgtgggatgt | aaatacaggt | 1080 |
| gaaatgctaa | acacgttgat | tcaccattgt | gaagcagttc | tgcacttgcg | tttcaataat | 1140 |
| ggcatgatgg | tgacctgctc | caaagatcgt | tccattgctg | tatgggatat | ggcctccca | 1200 |
| actgacatta | ccctccggag | ggtgctggtc | ggacaccgag | ctgctgtcaa | tgttgtagac | 1260 |
| tttgatgaca | agtacattgt | ttctgcatct | ggggatagaa | ctataaaggt | atgaacaca | 1320 |
| agtacttgtg | aatttgtaag | gaccttaaat | ggacacaaac | gaggcattgc | ctgtttgcag | 1380 |
| tacagggaca | ggctggtagt | gagtggctca | tctgacaaca | ctatcagatt | atgggacata | 1440 |

```
gaatgtggtg catgtttacg agtgttagaa ggccatgagg aattggtgcg ttgtattcga    1500
tttgataaca agaggatagt cagtggggcc tatgatggaa aaattaaagt gtgggatctt    1560
gtggctgctt tggaccccccg tgctcctgca gggacactct gtctacggac ccttgtggag    1620
cattccggaa gagttttcg actacagttt gatgaattcc agattgtcag tagttcacat    1680
gatgacacaa tcctcatctg ggacttccta aatgatccag ctgcccaagc tgaacccccc    1740
cgttcccctt ctcgaacata cacctacatc tccagataaa taaccataca ctgacctcat    1800
acttgcccag gacccattaa agttgcggta tttaacgtat ctgccaatac caggatgagc    1860
aacaacagta acaatcaaac tactgcccag tttccctgga ctagccgagg agcagggctt    1920
tgagactcct gttgggacac agttggtctg cagtcggccc aggacggtct actcagcaca    1980
actgactgct tcagtgctgc tatcagaaga tgtcttctat caattgtgaa tgattggaac    2040 ttttaaaccct cccctcctct cctcctttca cctctgcacc tagttttttc ccattggttc    2100
cagacaaagg tgacttataa atatatttag tgttttgcca gaaaaaaaaa a              2151
```

<210> SEQ ID NO 18
<211> LENGTH: 569
<212> TYPE: PRT
<213> ORGANISM: Homo sapiens

<400> SEQUENCE: 18

```
Met Asp Pro Ala Glu Ala Val Leu Gln Glu Lys Ala Leu Lys Phe Met
 1               5                  10                  15

Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
        35                  40                  45

Arg Leu Cys Leu Asn Gln Glu Thr Val Cys Leu Ala Ser Thr Ala Met
    50                  55                  60

Lys Thr Glu Asn Cys Val Ala Lys Thr Lys Leu Ala Asn Gly Thr Ser
65                  70                  75                  80

Ser Met Ile Val Pro Lys Gln Arg Lys Leu Ser Ala Ser Tyr Glu Lys
                85                  90                  95

Glu Lys Glu Leu Cys Val Lys Tyr Phe Glu Gln Trp Ser Glu Ser Asp
           100                 105                 110

Gln Val Glu Phe Val Glu His Leu Ile Ser Gln Met Cys His Tyr Gln
       115                 120                 125

His Gly His Ile Asn Ser Tyr Leu Lys Pro Met Leu Gln Arg Asp Phe
   130                 135                 140

Ile Thr Ala Leu Pro Ala Arg Gly Leu Asp His Ile Ala Glu Asn Ile
145                 150                 155                 160

Leu Ser Tyr Leu Asp Ala Lys Ser Leu Cys Ala Ala Glu Leu Val Cys
                165                 170                 175

Lys Glu Trp Tyr Arg Val Thr Ser Asp Gly Met Leu Trp Lys Lys Leu
            180                 185                 190

Ile Glu Arg Met Val Arg Thr Asp Ser Leu Trp Arg Gly Leu Ala Glu
        195                 200                 205

Arg Arg Gly Trp Gly Gln Tyr Leu Phe Lys Asn Lys Pro Pro Asp Gly
    210                 215                 220

Asn Ala Pro Pro Asn Ser Phe Tyr Arg Ala Leu Tyr Pro Lys Ile Ile
225                 230                 235                 240

Gln Asp Ile Glu Thr Ile Glu Ser Asn Trp Arg Cys Gly Arg His Ser
                245                 250                 255
```

-continued

```
Leu Gln Arg Ile His Cys Arg Ser Glu Thr Ser Lys Gly Val Tyr Cys
                260                 265                 270

Leu Gln Tyr Asp Asp Gln Lys Ile Val Ser Gly Leu Arg Asp Asn Thr
            275                 280                 285

Ile Lys Ile Trp Asp Lys Asn Thr Leu Glu Cys Lys Arg Ile Leu Thr
290                 295                 300

Gly His Thr Gly Ser Val Leu Cys Leu Gln Tyr Asp Glu Arg Val Ile
305                 310                 315                 320

Ile Thr Gly Ser Ser Asp Ser Thr Val Arg Val Trp Asp Val Asn Thr
                325                 330                 335

Gly Glu Met Leu Asn Thr Leu Ile His His Cys Glu Ala Val Leu His
            340                 345                 350

Leu Arg Phe Asn Asn Gly Met Met Val Thr Cys Ser Lys Asp Arg Ser
        355                 360                 365

Ile Ala Val Trp Asp Met Ala Ser Pro Thr Asp Ile Thr Leu Arg Arg
    370                 375                 380

Val Leu Val Gly His Arg Ala Ala Val Asn Val Val Asp Phe Asp Asp
385                 390                 395                 400

Lys Tyr Ile Val Ser Ala Ser Gly Asp Arg Thr Ile Lys Val Trp Asn
                405                 410                 415

Thr Ser Thr Cys Glu Phe Val Arg Thr Leu Asn Gly His Lys Arg Gly
            420                 425                 430

Ile Ala Cys Leu Gln Tyr Arg Asp Arg Leu Val Val Ser Gly Ser Ser
        435                 440                 445

Asp Asn Thr Ile Arg Leu Trp Asp Ile Glu Cys Gly Ala Cys Leu Arg
    450                 455                 460

Val Leu Glu Gly His Glu Glu Leu Val Arg Cys Ile Arg Phe Asp Asn
465                 470                 475                 480

Lys Arg Ile Val Ser Gly Ala Tyr Asp Gly Lys Ile Lys Val Trp Asp
                485                 490                 495

Leu Val Ala Ala Leu Asp Pro Arg Ala Pro Ala Gly Thr Leu Cys Leu
            500                 505                 510

Arg Thr Leu Val Glu His Ser Gly Arg Val Phe Arg Leu Gln Phe Asp
        515                 520                 525

Glu Phe Gln Ile Val Ser Ser Ser His Asp Asp Thr Ile Leu Ile Trp
    530                 535                 540

Asp Phe Leu Asn Asp Pro Ala Ala Gln Ala Glu Pro Pro Arg Ser Pro
545                 550                 555                 560

Ser Arg Thr Tyr Thr Tyr Ile Ser Arg
                565

<210> SEQ ID NO 19
<211> LENGTH: 6
<212> TYPE: PRT
<213> ORGANISM: Homo sapiens

<400> SEQUENCE: 19

Asp Ser Gly Leu Asp Ser
  1               5

<210> SEQ ID NO 20
<211> LENGTH: 20
<212> TYPE: PRT
<213> ORGANISM: Homo sapiens
```

```
<400> SEQUENCE: 20

Ala Ala Val Asn Val Val Asp Phe Asp Asp Lys Tyr Ile Val Ser Ala
1               5                   10                  15

Ser Gly Asp Arg
            20

<210> SEQ ID NO 21
<211> LENGTH: 17
<212> TYPE: PRT
<213> ORGANISM: Homo sapiens

<400> SEQUENCE: 21

Glu Leu Phe Pro Leu Ile Phe Pro Ala Glu Pro Ala Gln Ala Ser Gly
1               5                   10                  15

Pro

<210> SEQ ID NO 22
<211> LENGTH: 10
<212> TYPE: PRT
<213> ORGANISM: Homo sapiens
<220> FEATURE:
<221> NAME/KEY: MOD_RES
<222> LOCATION: (6)
<223> OTHER INFORMATION: PHOSPHORYLATION
<220> FEATURE:
<221> NAME/KEY: MOD_RES
<222> LOCATION: (10)
<223> OTHER INFORMATION: PHOSPHORYLATION

<400> SEQUENCE: 22

Cys Asp Arg His Asp Ser Gly Leu Asp Ser
1               5                   10

<210> SEQ ID NO 23
<211> LENGTH: 4
<212> TYPE: PRT
<213> ORGANISM: Homo sapiens

<400> SEQUENCE: 23

Val Val Asn Val
1

<210> SEQ ID NO 24
<211> LENGTH: 17
<212> TYPE: PRT
<213> ORGANISM: Homo sapiens

<400> SEQUENCE: 24

Ala Ala Val Asn Val Val Asp Phe Asp Asp Lys Tyr Ile Val Ser Ala
1               5                   10                  15

Ser

<210> SEQ ID NO 25
<211> LENGTH: 9
<212> TYPE: PRT
<213> ORGANISM: Homo sapiens

<400> SEQUENCE: 25

Leu Glu Gly His Glu Glu Leu Val Arg
1               5

<210> SEQ ID NO 26
<211> LENGTH: 12
<212> TYPE: PRT
<213> ORGANISM: Homo sapiens
```

```
<400> SEQUENCE: 26

Leu Val Val Ser Gly Ser Ser Asp Asn Thr Ile Arg
 1               5                  10

<210> SEQ ID NO 27
<211> LENGTH: 12
<212> TYPE: PRT
<213> ORGANISM: Homo sapiens

<400> SEQUENCE: 27

Ile Gln Asp Ile Glu Thr Ile Glu Ser Asn Trp Arg
 1               5                  10

<210> SEQ ID NO 28
<211> LENGTH: 9
<212> TYPE: PRT
<213> ORGANISM: Homo sapiens

<400> SEQUENCE: 28

Val Ile Ser Glu Gly Met Leu Trp Lys
 1               5

<210> SEQ ID NO 29
<211> LENGTH: 10
<212> TYPE: PRT
<213> ORGANISM: Homo sapiens
<220> FEATURE:
<221> NAME/KEY: MOD_RES
<222> LOCATION: (5)
<223> OTHER INFORMATION: PHOSPHORYLATION
<220> FEATURE:
<221> NAME/KEY: MOD_RES
<222> LOCATION: (9)
<223> OTHER INFORMATION: PHOSPHORYLATION

<400> SEQUENCE: 29

Asp Arg His Asp Ser Gly Leu Asp Ser Met
 1               5                  10

<210> SEQ ID NO 30
<211> LENGTH: 6
<212> TYPE: PRT
<213> ORGANISM: Homo sapiens
<220> FEATURE:
<221> NAME/KEY: MOD_RES
<222> LOCATION: (2)
<223> OTHER INFORMATION: PHOSPHORYLATION
<220> FEATURE:
<221> NAME/KEY: MOD_RES
<222> LOCATION: (6)
<223> OTHER INFORMATION: PHOSPHORYLATION

<400> SEQUENCE: 30

Asp Ser Gly Leu Asp Ser
 1               5
```